(12) United States Patent
Ye et al.

(10) Patent No.: US 11,629,357 B2
(45) Date of Patent: *Apr. 18, 2023

(54) DNA CONSTRUCTS FOR OBTAINING MARKER-FREE TRANSGENIC PLANTS

(71) Applicant: Monsanto Technology LLC, St. Louis, MO (US)

(72) Inventors: Xudong Ye, Chesterfield, MO (US); Larry A. Gilbertson, Chesterfield, MO (US); Shihshieh Huang, Woodland, CA (US); Susan J. Johnson, Creve Coeur, MO (US); Michael W. Petersen, Sauk City, WI (US); David Walters, North Stonington, CT (US); Paul S. Chomet, Mystic, CT (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/079,348

(22) Filed: Oct. 23, 2020

(65) Prior Publication Data

US 2021/0163977 A1    Jun. 3, 2021

Related U.S. Application Data

(60) Continuation of application No. 16/359,961, filed on Mar. 20, 2019, now abandoned, which is a division of application No. 15/376,495, filed on Dec. 12, 2016, now Pat. No. 10,240,165, which is a division of application No. 14/455,747, filed on Aug. 8, 2014, now Pat. No. 9,540,700, which is a division of application No. 13/558,336, filed on Jul. 25, 2012, now Pat. No. 8,829,275, which is a division of application No. 13/271,666, filed on Oct. 12, 2011, now Pat. No. 8,237,016, which is a division of application No. 11/747,824, filed on May 11, 2007, now Pat. No. 8,076,536.

(60) Provisional application No. 60/799,875, filed on May 12, 2006.

(51) Int. Cl.
    *C12N 15/82*    (2006.01)
    *C12N 9/10*     (2006.01)

(52) U.S. Cl.
    CPC ....... *C12N 15/8265* (2013.01); *C12N 15/821* (2013.01); *C12N 15/8205* (2013.01); *C12N 15/829* (2013.01); *C12N 15/8209* (2013.01); *C12N 15/8212* (2013.01); *C12N 15/8218* (2013.01); *C12N 15/8222* (2013.01); *C12N 15/8231* (2013.01); *C12N 15/8234* (2013.01); *C12N 15/8261* (2013.01); *C12N 15/8263* (2013.01); *C12N 15/8267* (2013.01); *C12N 15/8287* (2013.01); *C12N 15/8289* (2013.01); *C12N 15/8294* (2013.01); *C12N 9/1085* (2013.01)

(58) Field of Classification Search
    None
    See application file for complete search history.

(56) References Cited

U.S. PATENT DOCUMENTS

| | | | |
|---|---|---|---|
| 5,429,939 A | 7/1995 | Misawa et al. | |
| 5,545,816 A | 8/1996 | Ausich et al. | |
| 5,618,988 A | 4/1997 | Hauptmann. et al. | |
| 5,731,179 A | 3/1998 | Komari et al. | |
| 6,013,859 A | 1/2000 | Fabijanski et al. | |
| 6,307,123 B1 * | 10/2001 | Kriz .................. | C12N 15/8222 800/300 |
| 6,323,396 B1 | 11/2001 | Dirks et al. | |
| 6,429,356 B1 | 8/2002 | Shewmaker | |
| 6,458,594 B1 | 10/2002 | Baszczynski et al. | |
| 6,583,338 B2 | 6/2003 | McElroy et al. | |
| 7,078,588 B2 | 7/2006 | Wang et al. | |
| 7,238,514 B2 | 7/2007 | Matsuda et al. | |
| 7,288,694 B2 | 10/2007 | Armstrong et al. | |
| 7,575,917 B2 | 8/2009 | Gilbertson et al. | |
| 7,683,237 B2 | 3/2010 | Kriz et al. | |
| 8,076,536 B2 * | 12/2011 | Ye ...................... | C12N 15/8265 800/300 |
| 9,540,700 B2 * | 1/2017 | Ye ...................... | C12N 15/8294 |
| 2003/0110532 A1 | 6/2003 | Armostrong et al. | |
| 2006/0041956 A1 | 2/2006 | Lassner et al. | |
| 2006/0200878 A1 | 9/2006 | Lufiyya et al. | |

FOREIGN PATENT DOCUMENTS

| | | |
|---|---|---|
| CN | 1597969 | 2/2005 |
| CN | 1654662 | 8/2005 |
| EP | 0 687 730 | 12/1995 |
| EP | 792352 | 9/1997 |

(Continued)

OTHER PUBLICATIONS

Breitler et al, 2004, Transgenic Research 13: 271-287.*
de Pater et al, 1992, The Plant Journal 2: 837-844.*
Afolabi et al., "Novel pGreen/pSoup dual-binary vector system in multiple T-DNA co-cultivation as a method of producing marker-free (clean gene) transgenic rice (*Oryza sativa* L) plant," *African Journal of Biotechnology* 4(6):531-540; 2005.
An, "Development of Plant Promoter Expression Vectors and Their Use of Analysis of Differential Activity of Nopaline Synthase Promoter in Transformed Tobacco Cells", *Plant Physiol.* 81:86-91, 1986.
An et al., "New cloning vehicles for transformation of higher plants," *EMBO J.* 4(2); 277-284, 1985.

(Continued)

*Primary Examiner* — Jason Deveau Rosen
(74) *Attorney, Agent, or Firm* — Dentons US LLP; David Lanzotti

(57) ABSTRACT

The invention provides methods and compositions for identifying transgenic seed that contain a transgene of interest, but lack a marker gene. Use of an identification sequence that results in a detectable phenotype increases the efficiency of screening for seed and plants in which transgene sequences not linked to a gene of interest have segregated from the sequence encoding a gene of interest.

20 Claims, 23 Drawing Sheets
Specification includes a Sequence Listing.

(56) References Cited

FOREIGN PATENT DOCUMENTS

| | | |
|---|---|---|
| EP | 0911412 A1 | 4/1999 |
| JP | 9-154580 A | 6/1997 |
| JP | 10-327860 A | 12/1998 |
| JP | 2000-083666 A | 3/2000 |
| JP | 2000-342260 A | 12/2000 |
| JP | 2002-315460 A | 10/2002 |
| JP | 2003-000082 A | 1/2003 |
| JP | 5330231 | 8/2013 |
| WO | WO 95/16031 | 6/1995 |
| WO | WO 97/14807 | 4/1997 |
| WO | WO 97/41228 | 11/1997 |
| WO | WO 98/28430 | 7/1998 |
| WO | WO 2003/003816 | 1/2003 |
| WO | WO 03/101184 | 12/2003 |
| WO | WO 2004/092390 | 10/2004 |
| WO | WO 2004/099405 | 11/2004 |
| WO | WO 2005/079389 | 9/2005 |
| WO | WO 2005/120215 | 12/2005 |
| WO | WO 2006/017577 | 2/2006 |
| WO | WO 2007/134234 | 11/2007 |

OTHER PUBLICATIONS

Armstrong et al., "Conserved enzymes mediate the early reactions of carotenoid biosynthesis in nonphotosynthetic and photosynthetic prokaryotes," *Proc. Nat'l. Acad. Sci. USA* 87:9975-9979, 1990.
Bensmihen et al., "Analysis of an activated ABI5 allele using a new selection method for transgenic *Arabidopsis* seeds," *FEBS Letters*, 561:127-131; 2004.
Breitler et al., "A novel two T-DNA binary vector allows efficient generation of marker-free transgenic plants in three elite cultivars of rice (*Oryza sativa* L.)," *Transgenic Res.*, 13:271-287; 2004.
Caimi et al., "Fructan accumulation and sucrose metabolism in transgenic maize endosperm expressing a bacillus amyloliquefaciens sacB gene," *Plant Physiol.*, 110:355-363, 1996.
Carmi et al., "Induction of parthenocarpy in tomato via specific expression of the rolB gene in the ovary," *Planta*, 217:726-735; 2003.
Chen et al., "Green fluorescent protein as a vital elimination marker to easily screen marker-free transgenic progeny derived from plants co-transformed with a double T-DNA binary vector system," *Plant Cell Rep.*, 23:625-631; 2005.
Collens et al., "Development of auxotrophic agrobacterium tumefaciens for gene transfer in plant tissue culture," *Biotechnology Progress*, 20:890-896; 2004.
Dale et al., "Gene transfer and subsequent removal of the selection gene from the host genome," *Proc. Natl. Acad. Sci. USA*, 88:10558-10562; 1991.
De Block et al., "Two T-DNA's co-transformed into *Brassica napus* by a double *Agrobacterium tumefaciens* infections are mainly integrated at the same locus," *Theoretical and Applied Genetics* 82:257-263; 1991.
De Buck et al., "T-DNA vector backbone sequences are frequently integrated into the genome of transgenic plants obtained by agrobacterium-mediated transformation," *Molecular Breeding*, 6(5):459-468; 2000.
De Buck et al., "The DNA sequences of T-DNA junctions suggest that complex T-DNA loci are formed by a recombination process resembling T-DNA integration," *Plant J.*, 20:295-304;1999.
De Pater et al., "The promoter of the rice gene GOS2 is active in various different monocot tissues and binds rice nuclear factor ASF-1," *The Patent Journal*, vol. 2(6), pp. 837-844; 1992.
De Vetten et al., "A transformation method for obtaining marker-free plants of a cross-pollinating and vegetatively propagated crop," *Nat. Biotechnol.*, 21:439-442; 2003.
Dehesh et al., "KAS IV: a 3-ketoacyl-ACP synthase from *Cuphea* sp. Is a medium chain specific condensing enzyme," *The Plant Journal* 15(3) 383-390; 1998.

Ducreux et al., "Metabolic engineering of high carotenoid potato tubers containing enhanced levels of β-carotene and lutein," *J. of Exper. Botany*, 56:409:81-89, 2005.
Ebinuma et al., "Selection of marker-free transgenic plants using the isopentenyl transferase gene," *Proc. Natl. Acad. Sci. USA*, 94:2117-2121; 1997.
Fitzgibbon et al., "Cloning of a gene from *Pseudomonas* sp. strain PG2982 conferring increased glyphosate resistance," *Appl. Environ. Microbiol.*, 56(11):3382-3388, 1990.
Fraser et al., "Elevation of carotenoids in tomato by genetic manipulation," *J. Sci. Food Agric.*, 81:822-827; 2001.
GenBank Accession AB101655, Jan. 15, 2008.
GenBank Accession AB101656, Feb. 15, 2008.
GenBank Accession AB101657, Feb. 15, 2008.
GenBank Accession AE009418, May 28, 2004.
GenBank Accession AE009432, May 28, 2004.
GenBank Accession AF060518, Oct. 28, 1998.
GenBank Accession AF400123, Oct. 7, 2001.
GenBank Accession AM422760, Jan. 10, 2007.
GenBank Accession D83391, Sep. 21, 2002.
GenBank Accession L47479, Dec. 29, 1997.
GenBank Accession M15077, Apr. 26, 1993.
GenBank Accession M26194, Apr. 26, 1993.
GenBank Accession M38423, Apr. 11, 2001.
GenBank Accession M87280, Apr. 11, 2001.
GenBank Accession NC_003423, Jan. 25, 2008.
GenBank Accession NM_101474, Apr. 20, 2007.
GenBank Accession NM_119937, Apr. 20, 2007.
GenBank Accession NM_180024, Apr. 20, 2007.
GenBank Accession NM_180913, Apr. 20, 2007.
GenBank Accession NM_202110, Apr. 20, 2007.
GenBank Accession NM_202701, Apr. 20, 2007.
GenBank Accession NM_203251, Apr. 20, 2007.
GenBank Accession U12546, Apr. 6, 1995.
GenBank Accession U13043, Jun. 14, 2002.
GenBank Accession X14202, Jun. 12, 2006.
GenBank Accession X64255, Feb. 10, 1999.
GenBank Accession Y13658, Nov. 14, 2006.
Hajirezaei et al., "Inhibition of potato tuber sprouting: low levels of cytosolic pyrophosphate lead to non-sprouting tubers harvested from transgenic potato plants," *Potato Res.*, 42:353-372; 1999.
Halpin, "Gene stacking in transgenic plants—the challenge for the 21$^{st}$ century plant biotechnology," *Plant Biotechnol. J.*, 3:141-155, 2005.
Hanson et al., "A simple method to enrich an agrobacterium-transformed population for plants containing only T-DNA sequences," *Plant J.*, 19:727-734, 1999.
Hare et al., "Excision of selectable marker genes from transgenic plants," *Nature Biotechnol.*, 20:575-580; 2002.
He et al., "A T42M substitution in bacterial 5-enolpyruvylshikimate-3-phosphate synthase (EPSPS) generates enzymes with increased resistance to glyphosate," *Biosici Biotechnol Biochem.*, 67(6):1405-1409, 2003.
Hill et al., "A conserved domain of the viviparous-1 gene product enhances the DNA binding activity of the bZIP protein EmBP-1 and other transcription factors," *Journal of Biological Chemistry*, vol. 271, pp. 3366-3374; 1996.
Honeycutt et al., "Expression and inheritance of a shriveled-seed mutant in soybean," *Crop Science* 29(3):704-707; 1989.
Hong-Yan et al., "Generating marker-free transgenic tobacco plants by agrobacterium-mediated transformation with double T-DNA binary vector," *Acta Botanica Sinica*, 45:1103-1108; 2003.
Horsch et al., "Rapid assay of foreign gene expression in leaf discs transformed by agrobacterium tumefaciens: role of T-DNA borders in the transfer process," *PNAS USA*, 83:4428-4432; 1986.
Huang et al., "Generation of marker-free transgenic maize by regular two-border Agrobacterium transformation vectors," *Transgenic Research* 13(5):451-461; 2004.
Jianyue et al., "Introducing antisense waxy gene into rice seeds reduces grain amylose contents using a safe transgenic technique," *Chinese Science Bulletin*, vol. 50(1), pp. 39-44;2005.

(56) References Cited

OTHER PUBLICATIONS

Jofuku et al., "Control of seed mass and seed yield by the floral homeotic gene APETALA2," *Proc. Nat. Acad. Sci. USA*, 102:3117-3122; 2005.
Kalla et al., "The promoter of the barley aleurone-specific gene encoding a putative 7 kDa lipid transfer protein confers aleurone cell-specific expression in transgenic rice," *Plant Journal*, vol. 6, pp. 849-860; 1994.
Komari et al. "Vectors carrying two separate T-DNAs for co-transformation of higher plants mediated by agrobacterium tumefaciens and segregation of transformants free from selection markers," *The Plant J.*, 10(1):165-174; 1996.
Kononov et al., "Integration of T-DNA binary vector 'backbone' sequences into the tobacco genome: evidence for multiple complex patterns of integration," *Plant J.*, 11:945-957; 1997.
Krebbers et al., Determination of the Processing Sites of an *Arabidopsis* 2S Albumin and Characterization of the Complete Gene Family; *Plant Physiology* 87:859-866; 1988.
Kuraya et al., "Suppression of tranfer of non-T-DNA 'vector backbone' sequences by multiple left border repeats in vectors for transformation of higher plants mediated by agrobacterium tumefaciens," *Mol. Breeding*, 14:309-320, 2004.
Lonsdale et al., "The Effect of altered codon usage on luciferase activity in tobacco, maize and wheat," *Plant Cell Reports*; 17:396-399; 1998.
Lu et al., "Generation of selectable marker-free transgenic rice using double right-border (DRB) binary vectors," *Aust. J. Plant Physiol.*, 28:241-248; 2001.
Ludwig et al., "A Regulatory Gene as a Novel Visible Marker for Maize Transformation," *Science* 247:449-450, 1990.
Matthews et al., "Marker gene elimination from transgenic barley, using co-transformation with adjacent 'twin-T-DNAs' on a standard agrobacterium transformation vector," *Mol. Breeding*, 7:195-202; 2001.
McCormac et al., "Efficient co-transformation of nicotiana tabacum by two independent T-DNAs, the effect of T-DNA size and implications fro genetic separation," *Transgenic Res.*, 10:143-155; 2001.
McCormac et al., "pBECKS2000: a novel plasmid series for the facile creation of complex binary vectors, which incorporates "clean-gene" facilities," *Mol. Gen. Genet.*, 261:226-235; 1999.
Mendoza et al., "Leafy cotyledon 2 activation is sufficient to trigger the accumulation of oil and seed specific mRNAs in *Arabidopsis* leaves," *FEBS Letters*, 579:4666-4670; 2005.
Miki et al., "Selectable marker genes in transgenic plants: applications, alternatives and biosafety," *J. of Biotechnology*, 107:193-232; 2004.
Miller et al., "High efficiency transgene segregation in co-transformed maize plants using an Agrobacterium tumefaciens 2 T-DNA binary system," *Transgenic Research* 11(4):381-396; 2002.
Misawa et al., "Elucidation of the erwinia uredovora carotenoid biosynthetic pathway by functional analysis of gene products expressed in *Escherichia coli*," *J. Bacteriol.*, 172:6704-6712; 1990.
Mizukami et al., "Plant organ size control: Ainteguumenta regulates growth and cell numbers during organogenesis," *Proc. Natl. Acad. Sci. USA*, 97:942-947; 2000.
Morello et al., "Overexpression of the calcium-dependent protein kinase OsCDPK2 in transgenic rice is expressed by light in leaves and disrupts seed development," *Transgenic Res.*, 9:453-462, 2000.
Ow et al., "Transient and stable expression of the firefly luciferase gene in plant cells and transgenic plants," *Science*, 234:856-859; 1986.
Park et al., "Co-transformation using a negative selectable marker gene for the production of selectable marker gene-free transgenic plants," *Theor. Appl. Genet.*, 109:1562-1567; 2004.
Parkhi et al., "Molecular characterization of marker-free transgenic lines of indica rice that accumulate carotenoids in seed endosperm," *Mol. Gen. Genomics*, 274:325-336; 2005.

Patterson et al., "Genetic Analysis of B-Peru, a Regulatory Gene in Maize," *Genetics* 127(1) 205-220; 1991 Abstract Only.
Puchta, "Marker-free transgenic plants," *Pl. Cell Tiss. Org. Cult.*, 74:123-143; 2003.
Radchuk et al., "Repressing the expression of the sucrose nonfermenting-1-related protein kinase gene in pea embryo causes pleiotropic defects of maturation similar to an abscisic acid-insensitive phenotype," *Plant Physiol.*, 140:263-278; 2006.
Ramanathan et al., "Transfer of non-T-DNA portions of agrobacterium tumefaciens Ti plasmid pTiA6 from the left terminus of $T_L$-DNA," *Plant Molecular Biology*, 28:1149-1154, 1995.
Rotino et al., "Genetic engineering of parthenocarpic plants," *Nat. Biotechnol.*, 15:1398-1401; 1997.
Russell et al., "Tissue-specific expression in transgenic maize of four endosperm promoters from maize and rice," *Transgenic Research*, vol. 6, pp. 157-168, 1997.
Rutherford et al., "Improved transcriptional activators and their use in mis-expression traps in *Arabidopsis*," The Plant Journal 43:769-788, 2005.
Sandmann et al., "New functional assignment of the carotenogenic genes crtB and crtE with constructs of these genes from *erwinia* species," *FEMS Microbiol Lett.*, 69(3):253-257, 1992.
Sato et al., "Production of γ-linolenic acid and stearidonic acid in seeds of marker-free transgenic soybean," *Crop Sci.*, 44:646-652; 2004.
Schruff et al., "The auxin response factor 2 gene of *Arabidopsis* links auxin signalling, cell division, and the size of seeds and other organs," *Development*, 133:251-261; 2006.
Scutt et al., "Techniques for the removal of marker genes from transgenic plants," *Biochimie*, 84:1119-1126; 2002.
Segal et al., "A New Opaque Variant of Maize by a Single Dominant RNA-Interference-Inducing Transgene," *Genetics* 165:387-397, 2003.
Shewmaker et al., "Seed-specific overexpression of phytoene synthase: increase in carotenoids and other metabolic effects," *The Plant J.*, 20(4):401-412; 1999.
Stone et al., "Leafy COTYLEDON2 encodes a B3 domain transcription factor that induces embryo development," *PNAS* 98(20): 11806-11811; 2001.
Straub et al., "Structure and promoter analysis of an ABA- and stress-regulated barley gene, HVA1," *Plant Molecular Biology*, vol. 26, pp. 617-630; 1994.
Wang et al., Expression of a bacterial aroA mutant, aroA-M1, encoding 5-enolpyruvylshikimate-3-phosphate synthase for the production of glyphosate-resistant tobacco plants. *J. Plant Res.*, 116(6):455-460; 2003.
Wei et al., "Fluorescent screening of transgenic arabidopsis seeds without germination," *Plant Physiol.*, 135:709-714; 2004.
Wenck et al., "Reef-coral proteins as visual, non-destructive reporters for plant transformation," *Plant Cell Rep.*, 22:244-251; 2003.
Wildt et al., "cobA, a red fluorescent transcriptional reporter for *Escherichia coli*, yeast, and mammalian cells," *Nature Biotechnology* 17:1175-1178, 1999.
Xing et al., "The use of the two T-DNA binary system to derive marker-free transgenic soybeans," *In vitro Cellular and Developmental Biology Plant* 36(6):456-463; 2000.
Xue et al., "Selectable marker-free transgenic barley producing high level of cellulase (1,4-β-glucanase) in developing grains," *Plant Cell Rep.*, 21:1088-1094; 2003.
Yoder et al., "Transformation systems for generating marker-free transgenic plants," *Bio/Technology*, 12:263-267; 1994.
Sequence US-13-271-666-2;Hauptmann et al. Locus 140224 from U.S. Pat. No. 5,618,988; 1997.
Translation of Office Action dated Jan. 8, 2013, in Japanese Application No. JP 2009-511185.
Office Action regarding Canadian Application No. 2,917,552, dated Sep. 8, 2016.
Twell, D. Protoplasma 187: 144-154 (1995).
Muschietti et al. The Plant Journal 6(3): 321-338 (1994).
Chen et al. Plant Biotechnology Journal 4: 477-487 (2006).

\* cited by examiner

| | 46611 | 46612 | 46613 | 46614 | 46615 | 46616 | 46622 | 46623 | 46624 | 46868 | 46870 | 47266 | 47267 |
|---|---|---|---|---|---|---|---|---|---|---|---|---|---|
| Shrunken seeds | 8 | 8 | 0 | 8 | 8 | 8 | 0 | 8 | 1 | 1 | 8 | 8 | 16 |
| Normal seeds | 8 | 8 | 16 | 8 | 8 | 8 | 10 | 8 | 15 | 15 | 8 | 8 | 0 |
| Total | 16 | 16 | 16 | 16 | 16 | 16 | 10 | 16 | 16 | 16 | 16 | 16 | 16 |
| GUS–Shrunken | 7 | 5 | 0 | 8 | 8 | 7 | 0 | 8 | 1 | 1 | 8 | 8 | 0 |
| GUS–Normal | 2 | 0 | 0 | 2 | 0 | 7 | 0 | 8 | 0 | 2 | 8 | 4 | 2 |
| Total GUS pos | 9 | 5 | 0 | 10 | 8 | 14 | 0 | 16 | 1 | 3 | 16 | 12 | 2 |
| Ratio 1 | 0.875 | 0.625 | 0 | 1 | 1 | 0.875 | 0 | 1 | 1 | 1 | 1 | 1 | 0 |
| Ratio 2 | 0.25 | 0 | 0 | 0.25 | 0 | 0.875 | 0 | 1 | 0 | 0.1333 | 1 | 0.5 | 0 |
| Ratio 3 | 0.5625 | 0.3125 | 0 | 0.625 | 0.5 | 0.875 | 0 | 1 | 0.0625 | 0.1875 | 1 | 0.75 | 0.125 |

Ratio 1: GUS positive of shrunken seeds  Very weak
Ratio 2: GUS positive of normal seeds
Ratio 3: GUS positive of total 16 seeds chipped Linked
Negative plants
Either totally linked or negative lines
Segregating lines, they could be either single copy or multiple copy lines for GUS staining normal seeds are very weak.

Three lines (46614, 46868, and 47267) GUS staining normal seeds are very weak. gene of interest positive, marker-free

| Standard 2T | 2T w/crtB label-linked Marker |
|---|---|
| 100 events | 100 events |
| 69 (after GOI screen) | 69 (after GOI screen) |
| 45 (after low copy) | 45 (after low copy) |
| 14 (after linkage Southern) | 45 (no linkage Southern) |
| 14 (no germline determination) | 38 (after germline determination from crtB) |
| 14 events to R1 | 38 events to R1 |
| 1050 progeny planted (75/event) | 722 progeny planted (19 yellow seed/event) |
| 1050 for glyphosate spray | No glyphosate spray |
| 263 for zygosity testing | 722 for zygosity testing |

FIG. 8

SEQUENCE LISTING

<160> NUMBER OF SEQ ID NOS: 3

<210> SEQ ID NO 1
<211> LENGTH: 1048
<212> TYPE: DNA
<213> ORGANISM: Artificial Sequence
<220> FEATURE:
<223> OTHER INFORMATION: Description of Artificial Sequence: Artificial Primer

<400> SEQUENCE: 1 ccacacccttaggtaacccagtagatccagaggaattcattatcagtgcaattgttttgt    60

| | | |
|---|---|---|
| cacgatcaaa ggactctggt acaaaatcgt attcattaaa accgggaggt agatgagatg | 120 | |
| tgacgaacgt gtacatcgac tgaaatccct ggtaatccgt tttagaatcc atgataataa | 180 | |
| ttttctggat tattggtaat ttttttttgca cgttcaaaat tttttgcaac ccctttttgg | 240 | |
| aaacaaacac tacggtaggc tgcgaaatgt tcatactgtt gagcaattca cgttcattat | 300 | |
| aaatgtcgtt cgcgggcgca actgcaactc cgataaataa cgcgcccaac accggcataa | 360 | |
| agaattgaag agagttttca ctgcatacga cgattctgtg atttgtattc agcccatatc | 420 | |
| gacgcgtgaa gacgccaaaa acataaagaa aggcccggcg ccattctatc ctctagagga | 480 | |
| tggaaccgct ggagagcaac tgcataaggc tatgaagaga tacgccctgg ttcctggaac | 540 | |
| aattgctttt acagatgcac atatcgaggt gaacatcacg tacgcggaat acttcgaaat | 600 | |
| gtccgttcgg ttggcagaag ctatgaaacg atatgggctg aatacaaatc acagaatcgt | 660 | |
| cgtatgcagt gaaaactctc ttcaattctt tatgccggtg ttgggcgcgt tatttatcgg | 720 | |
| agttgcagtt gcgcccgcga acgacattta taatgaacgt gaattgctca acagtatgaa | 780 | |
| catttcgcag cctaccgtag tgtttgtttc caaaaagggg ttgcaaaaaa ttttgaacgt | 840 | |
| gcaaaaaaaa ttaccaataa tccagaaaat tattatcatg gattctaaaa cggattacca | 900 | |
| gggatttcag tcgatgtaca cgttcgtcac atctcatcta cctcccggtt ttaatgaata | 960 | |
| cgattttgta ccagagtcct ttgatcgtga caaacaatt gcactgataa tgaattcctc | 1020 | |
| tggatctact gggttaccta agggtgtg | 1048 | |

<210> SEQ ID NO 2
<211> LENGTH: 930
<212> TYPE: DNA
<213> ORGANISM: Artificial Sequence
<220> FEATURE:
<223> OTHER INFORMATION: Description of Artificial Sequence: Artificial Primer

<400> SEQUENCE: 2

| | | |
|---|---|---|
| atgtcccagc ctcctctcct ggatcatgct acccaaacta tggctaacgg tagcaagtcc | 60 | |
| ttcgctaccg ccgctaagct cttcgatcct gctactaggc gttccgtcct catgctgtac | 120 | |
| acctggtgta ggcattgcga cgatgtgatc gacgatcaaa cccacggttt cgcgtccgag | 180 | |
| gctgcggccg aggaagaggc gacccaaagg ctcgctcgcc tccgtaccct caccctcgcc | 240 | |
| gctttcgagg gcgctgagat gcaagatcct gcgttcgccg cttccaagaa ggtcgccctc | 300 | |
| acccacggca tcactccaag gatggccctg gaccacctgg acggtttcgc tatggacgtc | 360 | |
| gcccaaactc gctacgtgac tttcgaggac actctccggt actgctacca gtcgccggt | 420 | |
| gttgtcggcc tcatgatggc gcgcgtcatg ggtgtccgcg acgagcgcgt cctcgacagg | 480 | |
| gcttgcgacc tcggcctcgc gtttcagctt accaacattg ctagggacat catcgacgac | 540 | |
| gctgcgatag ataggtgtta cctgcctgct gagtggcttc aggacgctgg tcttacgccc | 600 | |
| gagaactacg ctgccaggga gaacagggct gcccttgcta gagtcgctga gcgtttgatc | 660 | |
| gacgcggctg aaccctatta cattagctcg caagcgggtt tgcatgactt gcctccacgt | 720 | |
| tgtgcgtggg ccattgcgac ggcgcgtagt gtttatcgtg aaattgggat caaggttaag | 780 | |
| gccgctggag gatcagcatg ggaccggaga cagcatacgc taagggaga gaagatcgca | 840 | |
| atgctaatgg cagctcccgg ccaagtcatc cgcgcaaaga caacgcgggt tacacccaga | 900 | |
| ccagcgggct tatggcagcg accagtatga | 930 | |

<210> SEQ ID NO 3

```
<211> LENGTH: 930
<212> TYPE: DNA
<213> ORGANISM: Artificial Sequence
<220> FEATURE:
<223> OTHER INFORMATION: Description of Artificial Sequence:  Artificial
      Primer

<400> SEQUENCE: 3
atgtcccagc ctcctctcct ggatcatgct acccaaacta tggctaacgg tagcaagtcc      60
ttcgctaccg ccgctaagct cttcgatcct gctactaggc gttccgtcct catgctgtac     120
acctggtgta ggcattgcga cgatgtgatc gacgatcaaa cccacggttt cgcgtccgag     180
gctgcggccg aggaagaggc gacccaaagg ctcgctcgcc tccgtaccct caccctcgcc     240
gctttcgagg gcgctgagat gcaagatcct gcgttcgccg ctttccaaga ggtcgccctc     300
acccacggca tcactccaag gatggccctg gaccacctgg acggtttcgc tatggacgtc     360
gcccaaactc gctacgtgac tttcgaggac actctccggt actgctacca tgtcgccggt     420
gttgtcggcc tcatgatggc gcgcgtcatg ggtgtccgcg acgagcgcgt cctcgacagg     480
gcttgcgacc tcggcctcgc gtttcagctt accaacattg ctagggacat catcgacgac     540
gctgcgatag ataggtgtta cctgcctgct gagtggcttc aggacgctgg tcttacgccc     600
gagaactacg ctgccaggga gaacagggcc gcccttgcta gagtcgctga gcgtttgatc     660
gacgcggctg aaccctatta cattagctcg caagcgggtt tgcatgactt gcctccacgt     720
tgtgcgtggg ccattgcgac ggcgcgtagt gtttatcgtg aaattgggat caaggttaag     780
gccgctggag gatcagcatg ggaccggaga cagcatacgt ctaagggaga gaagatcgca     840
atgctaatgg cagctcccgg ccaagtcatc cgcgcaaaga caacgcgggt tacacccaga     900
ccagcgggct tatggcagcg accagtatga                                      930
```

DNA CONSTRUCTS FOR OBTAINING MARKER-FREE TRANSGENIC PLANTS

This application is a continuation of U.S. application Ser. No. 16/359,961, filed Mar. 20, 2019, which is a divisional of U.S. application Ser. No. 15/376,495, filed Dec. 12, 2016, now U.S. Pat. No. 10,240,165, which is a divisional of U.S. application Ser. No. 14/455,747, filed Aug. 8, 2014, now U.S. Pat. No. 9,540,700, which is a divisional of U.S. application Ser. No. 13/558,336, filed Jul. 25, 2012, now U.S. Pat. No. 8,829,275, which is a divisional of U.S. application Ser. No. 13/271,666, filed Oct. 12, 2011, now U.S. Pat. No. 8,237,016, which is a divisional of U.S. application Ser. No. 11/747,824, filed May 11, 2007, now U.S. Pat. No. 8,076,536, which claims the priority of U.S. Provisional Application Ser. No. 60/799,875, filed May 12, 2006, the entire disclosures of which are incorporated herein by reference.

BACKGROUND OF THE INVENTION

1. Field of the Invention

The invention generally relates to transgenic plants. More specifically, the invention relates to identification and removal of unwanted or unnecessary DNA in transformed plants.

2. Description of Related Art

The identification of unnecessary or unwanted transgenic DNA in transformed plants has been the subject of numerous investigations and many different methods have been examined in efforts to eliminate these transgenic sequences from such plants (e.g. Hanson et al., 1999; Dale et al., 1991; Ebinuma et al., 1997; Yoder et al., 1994; Kononov et. al., 1997; Hare and Chua, 2002; Scutt et al., 2002; Puchta, 2003; de Vetten et al., 2003; Halpin, 2005; U.S. Published Appln. 20030110532; U.S. Published Appln. 20040237142; U.S. Pat. No. 6,458,594). In general, it is beneficial to identify plants that do not include transgenic DNA not contributing to an agronomically useful trait of the transgenic plant.

Many methods for introducing transgenes in plants by Agrobacterium-mediated transformation utilize a T-DNA (transferred DNA) that incorporates a transgene and associated genetic elements, and transfers these into the genome of a plant. Generally, the transgene(s) is bordered by a right border DNA molecule (RB) and a left border DNA molecule (LB), and is transferred into the plant genome, integrating at one or more loci. It has been observed that when a DNA construct contains more than one T-DNA, these T-DNAs and the transgenes contained within may be integrated into the plant genome at separate loci (Framond et al., 1986). This is referred to as co-transformation.

The process of co-transformation can be achieved by delivery of the T-DNAs with a mixture of Agrobacterium strains transformed with plasmids carrying the separate T-DNAs. Co-transformation can also be achieved by transforming one Agrobacterium strain with two or more DNA constructs, each containing one T-DNA. An additional method employs two T-DNAs on a single DNA vector and identifying transgenic cells or plants that have integrated the T-DNAs at different loci. In a non-Agrobacterium-mediated transformation system, such as a physical method for introducing DNA including bombardment with microprojectiles, two DNA molecules could be integrated independently into the target genome, and then segregate independently in a subsequent generation. Use of 2 T-DNA constructs allowing for independent insertion of sequences and their genetic segregation, has also been described (e.g. U.S. Pat. No. 5,731,179; Zhou et al., 2003; Breitler et al., 2004; Sato et al., 2004). While the foregoing has furthered the understanding in the art, there remains a need for improved methods and compositions for obtaining marker free plants to make product development more efficient. Previously described screening processes have been highly labor intensive, for instance requiring Southern blot or PCR™ analysis following growth of R0 and/or R1 plant material.

U.S. Publication 20060041956 describes use of a visual marker gene in conjunction with Agrobacterium-mediated transformation. However, the publication does not describe any method where such markers are linked to a selectable or screenable marker gene and unlinked to a gene of interest. Thus, there remains a great need in the art for methods and compositions that would improve the ease and efficiency with which plants lacking marker sequences and/or other transgenic DNA which is not agronomically useful can be identified and eliminated.

SUMMARY OF THE INVENTION

In one aspect, the invention provides a method of preparing marker-free seeds from a transgenic plant comprising the steps of: a) obtaining seeds of a transgenic plant transformed with a first DNA segment comprising a nucleic acid of interest and a second DNA segment comprising a plant marker gene physically and/or genetically linked to a DNA cassette that is operably linked to a promoter functional in the seed, wherein the DNA cassette confers a detectable phenotype to seeds that comprise the DNA cassette; b) screening the seeds for the absence of the detectable phenotype; and c) selecting at least a first seed that lacks the detectable phenotype to obtain a seed that is free of the marker gene. In one embodiment, step c) further comprises assaying the seed for the presence of the nucleic acid of interest and selecting a seed that comprises the nucleic acid of interest and lacks the selectable marker gene. In certain embodiments, the marker gene is a selectable or screenable marker gene.

In certain embodiments, the DNA cassette may be translationally or transcriptionally fused to the selectable marker gene; that is, it may encode an RNA that is translationally or transcriptionally fused to the selectable marker gene. In a further embodiment the DNA cassette comprises an antisense or sense DNA fragment with at least 19 or 21 bp of homology to an endogenous gene, for instance wherein the antisense or sense DNA fragment is operably linked to a promoter functional in a seed. In yet another embodiment, the DNA cassette comprises a pair of inverted repeats of a DNA fragment, wherein each fragment is at least 19 or 21 bp in size, and wherein the DNA fragment is homologous to an endogenous gene, operably linked to a promoter functional in the seed. The inverted DNA fragment repeat homologous to an endogenous gene may also be embedded in an intron within the selectable marker gene. In certain embodiments, the DNA cassette encodes a sense or antisense RNA comprising at least 19 or 21 nucleotides wherein the DNA fragment is homologous to an endogenous gene.

In a method of preparing marker-free seeds according to the invention, seed selected may lack a screenable or screenable gene and DNA cassette. Obtaining seeds of a transgenic plant may comprise transforming or co-transforming the transgenic plant or a progenitor thereof of any previous generation with first and second DNA segments on separate DNA constructs. Obtaining seeds of a transgenic plant may also comprise transforming the transgenic plant or a progenitor thereof of any previous generation with a single DNA construct comprising the first and second DNA segments. First and second DNA segments may be bounded by different T-DNA border sequences. In a method of the invention, a transgenic plant may be produced by transforming the plant or a progenitor thereof of any previous generation with a DNA construct comprising (i) the first DNA segment flanked by left and right T-DNA borders, and (ii) the second DNA segment flanked by a second set of left and right T-DNA borders, wherein the second DNA segment further comprises a selectable marker gene operably linked to a promoter functional in the transgenic plant. The first and second DNA segments may or may not be genetically linked in the transgenic plant.

Transgenic plants used according to the invention may be produced by introducing first and second DNA segments into the plant or a progenitor thereof of any previous generation by transformation mediated by a bacterial strain selected from the genus *Agrobacterium, Rhizobium, Mesorhizobium,* or *Sinorhizobium*. The transgenic plants may also be produced, for example, by microprojectile bombardment.

A selectable marker used with the invention may encode a product selected from the group consisting of CP4 EPSPS, bar, DMO, NptII, glyphosate acetyl transferase, mutant acetolactate synthase, methotrexate resistant DHFR, dalapon dehalogenase, PMI, Protox, hygromycin phosphotransferase and 5-methyl tryptophan resistant anthranilate synthase. A DNA cassette sequence for use with the invention may be selected, for example, from the group consisting of crtB, gus, gfp, sacB, lux, an anthocyanin synthesis gene, DefH9-iaaM rolB, OsCDPK2, AP2, AFR2, ANT transcription factor, LEC2, Snf-1, cobA, KAS4, splA, zein inverted repeats, B-peru, and yeast ATP-PFK. The cassette may be operably linked to a promoter functional in a tissue selected from an embryo, seed endosperm, cotyledon, aleurone, and seed coat. The promoter may be, for example, selected from the group consisting of a napin promoter, a beta-phaseolin promoter, a beta-conglycinin subunit promoter, a zein promoter, an Osgt-1 promoter, an oleosin promoter, a starch synthase promoter, a globulin 1 promoter, a barley LTP2 promoter, an alpha-amylase promoter, a chitinase promoter, a beta-glucanase promoter, a cysteine proteinase promoter, a glutaredoxin promoter, a HVA1 promoter, a serine carboxypeptidase II promoter, a catalase promoter, an alpha-glucosidase promoter, a beta-amylase promoter, a VP1 promoter, a USP promoter, USP88 promoter, USP99 promoter, Lectin, and a bronze2 promoter. The detectable phenotype may be assayed by detection of a catalytic activity. The detectable phenotype may be selected from the group consisting of seed color, seed opacity, seed germinability, seed size, seed viability, seed shape, seed texture, and a defective or aborted seed. Screening of seeds may be done by an automated seed sorting machine.

In another aspect, the invention provides a DNA construct comprising (a) a first DNA segment comprising left and right T-DNA borders flanking a gene of interest operably linked to a promoter functional in plants, and (b) a second DNA segment comprising a second set of left and right T-DNA borders flanking a promoter functional in a seed operably linked to a DNA cassette that confers a detectable phenotype in seeds comprising the DNA cassette and a selectable marker gene operably linked to a promoter functional in plants. The gene of interest may confer a trait selected from the group consisting of herbicide tolerance, insect or pest resistance, disease resistance, increased biomass, modified fatty acid metabolism, modified carbohydrate metabolism, and modified nutritional quality. In the construct, the DNA cassette and selectable marker gene may be operably linked to the same promoter. In one embodiment, the DNA cassette and the selectable marker gene are operably linked to different promoters. In specific embodiments, the selectable marker gene encodes a product selected from the group consisting of CP4 EPSPS, phosphinothricin acetyltransferase, DMO, NptII, glyphosate acetyl transferase, mutant acetolactate synthase, methotrexate resistant DHFR, dalapon dehalogenase, PMI, Protox, hygromycin phosphotransferase and 5-methyl tryptophan resistant anthranilate synthase. In another embodiments, the DNA cassette is selected from the group consisting of crtB, gus, gfp, sacB, lux, an anthocyanin synthesis gene, DefH9-iaaM, rolB, OsCDPK2, AP2, AFR2, ANT transcription factor, LEC2, Snf-1, cobA, KAS4, splA, zein inverted repeats, B-peru, and yeast ATP-PFK. The DNA cassette may be operably linked to a promoter functional in a tissue selected from the group consisting of an embryo, seed endosperm, cotyledon, aleurone, and seed coat. In one embodiment, the DNA cassette is operably linked to a promoter selected from the group consisting of a napin promoter, a beta-phaseolin promoter, a beta-conglycinin subunit promoter, a zein promoter, an Osgt-1 promoter, an oleosin promoter, a starch synthase promoter, a globulin 1 promoter, a barley LTP2 promoter, an alpha-amylase promoter, a chitinase promoter, a beta-glucanase promoter, a cysteine proteinase promoter, a glutaredoxin promoter, a HVA1 promoter, a serine carboxypeptidase II promoter, a catalase promoter, an alpha-glucosidase promoter, a beta-amylase promoter, a VP1 promoter, a USP88 or USP99 promoter, and a bronze2 promoter.

In yet another aspect, the invention provides transgenic cells and plants transformed with a construct provided herein. In one embodiment, a transgenic plant is provided that is co-transformed with a DNA construct containing a first DNA segment comprising left and right T-DNA borders flanking a gene of interest operably linked to a promoter functional in plants and a second DNA construct containing a second DNA segment comprising a second set of left and right T-DNA borders flanking a promoter functional in a seed operably linked to a DNA cassette that confers a detectable phenotype in seeds comprising the DNA cassette and a selectable marker gene operably linked to a promoter functional in plants. Cells of such a plant are also provided.

In still yet another aspect, the invention provides a DNA construct comprising right and left T-DNA borders, wherein a first DNA segment comprising a gene of interest operably linked to a promoter functional in plants is located after the right border and a second DNA segment comprising a DNA cassette that confers a detectable phenotype to plant seeds that comprise the DNA cassette and a marker gene, such as a selectable marker gene, operably linked to a promoter functional in plants is located after the left border.

In still yet another aspect, the invention provides a DNA construct comprising right and left T-DNA borders, wherein a first DNA segment comprising a DNA cassette that confers a detectable phenotype to plant seeds that comprise the DNA cassette and a selectable marker gene operably linked to a promoter functional in plants is located after the right border and a second DNA segment comprising a gene of interest operably linked to a promoter functional in plants is located after the left border.

In still yet another aspect, the invention provides a DNA construct containing two right T-DNA borders, wherein a first DNA segment comprising a gene of interest operably linked to a promoter functional in plants is located after one right border and a second DNA segment comprising a DNA cassette that confers a detectable phenotype to plant seeds that comprise the DNA cassette and a selectable marker gene operably linked to a promoter functional in plants located after the other right border.

In yet another aspect, the invention provides an isolated nucleic acid sequence comprising SEQ ID NO:2, SEQ ID NO:3, or a sequence with at least 70%, 75%, 85%, or 95% identity to SEQ ID NO:2 or SEQ ID NO:3, and encoding a polypeptide with phytoene synthase activity. In one embodiment, the invention also provides a recombinant DNA construct comprising a nucleic acid sequence of SEQ ID NO:2 or SEQ ID NO:3, or a recombinant DNA construct comprising a sequence with at least 71%, 80%, 90%, 95%, 98%, or 99% identity to SEQ ID NO:2 or SEQ ID NO:3, and encoding a polypeptide with phytoene synthase activity, operably linked to a heterologous promoter functional in a plant. A host cell comprising such a sequence, wherein the cell is a bacterial cell or a plant cell is another embodiment of the invention. In another embodiment, the invention provides a transgenic plant or seed comprising SEQ ID NO:2 or SEQ ID NO:3 SEQ ID NO:2, SEQ ID NO:3, or a sequence with at least 71%, 80%, 90%, 95%, 98%, or 99% identity to SEQ ID NO:2 or SEQ ID NO:3, and encoding a polypeptide with phytoene synthase activity.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 6. GUS staining of pMON67465 seed.

FIG. 7. CP4 & CrtB PCR on GUS positive seeds.

FIG. 8. Comparison of linkage-Southern and screenable-marker approaches for screening transgenic events.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The invention overcomes deficiencies in the prior art by providing constructs and methods allowing for efficiently distinguishing seeds lacking an identification sequence and marker-gene sequence, but including a gene or genes of interest (GOI), from seeds that contain an identification gene sequence and marker-gene sequence, based on a phenotype conferred by a seed-expressed identification gene, sequence, or cassette. In particular, the present invention provides, in one embodiment, transformation constructs and methods for transformation of plant cells which include: (i) a gene of interest; and (ii) an identification sequence expressed in seed and physically linked to a selectable or screenable marker gene that may be expressed in various plant tissues, wherein the construct and/or transformation method is designed so that the genetic elements of (i) and (ii) can integrate independently into the plant genome, and thus genetically segregate from each other.

The expression or lack thereof of the identification sequence in seed tissues allows for direct identification of seeds and plants that lack the seed-expressed identification sequence and the physically linked selectable or screenable marker gene, while allowing for choice of seed and plants still containing the transgene of interest. Choosing seed including the gene of interest and lacking marker-gene sequences at the seed level represents a significant advance in that it avoids the need for previously utilized screening methods that are comparatively cost and labor intensive. Additionally, time may be saved as screening can be done prior to or during germination without requiring growth of the next generation of plants to a size permitting tissue harvest, as needed for linkage-Southern analysis, for example.

Figure 21:
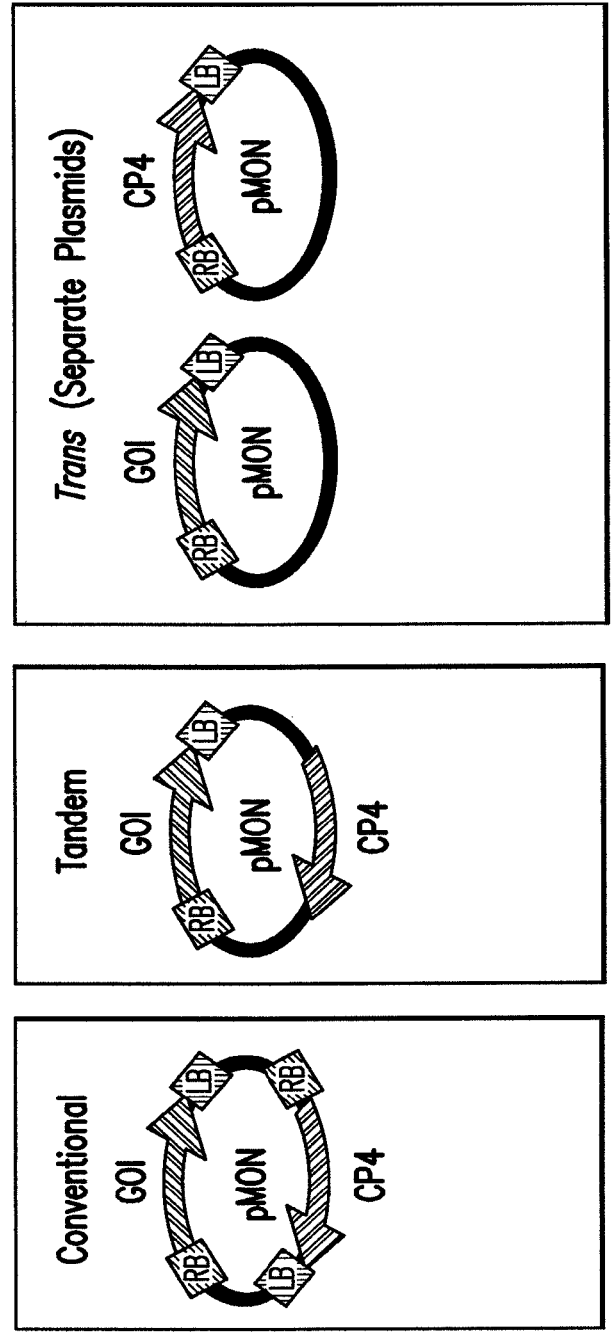
FIG. 21. 2 T-DNA vector formats—schematic diagram.

In one embodiment, transformation of plant tissue is performed by an *Agrobacterium* or other *Rhizobia*-mediated method (See e.g., U.S. Provisional Patent Application Ser. No. 60/800,872, filed May 16, 2006, entitled "Use of Non *Agrobacterium* Bacterial Species for Plant Transformation", the entire disclosure of which is specifically incorporated herein by reference), and the DNA sequences including the identification sequence expressed in seed and the physically linked selectable or screenable marker gene are present together on a T-DNA or other sequence (e.g., vector backbone) that is transferred into a plant cell (e.g. flanked by T-DNA RB and/or LB sequences or without a border sequence). The identification sequence and marker gene may be transferred to the plant physically linked, while the gene of interest is present on a separate T-DNA flanked by its own RB and LB sequences, or other sequence transferred into a plant cell, and can be integrated at an independent locus (e.g. FIG. 21). The selectable and/or screenable marker permits identification of transformed plant tissues. Fertile plants can be obtained and selfed or crossed in a breeding scheme in order to follow segregation of phenotypes in the next generation. Strategies for performing such breeding are well known in the art, and may vary in details between different plants. Seed expression, or lack of expression, of the identification sequence permits facile identification of seed with respect to the presence of marker and identification sequences. The gene of interest, for example, may contain at least one plant expression cassette encoding a trait selected from the group consisting of herbicide tolerance, antibiotic resistance, insect resistance, disease resistance, stress resistance (e.g., drought and cold), enhanced nutrient use efficiency, enhanced nutritive content (e.g., amino acid, protein, sugars, carbohydrates, fatty acids, and/or oil), sterility systems, industrial enzymes (e.g., pharmaceuticals and processing enzymes for bio-fuels) and enhanced yield.

The sequences that may be transferred into a plant cell (e.g. T-DNAs) may be present on one transformation vector in a bacterial strain being utilized for transformation. In another embodiment, the sequences including the identification sequence and plant selectable marker, and the sequence(s) comprising the gene(s) of interest may be present on separate transformation vectors in the bacterial strain. In yet another embodiment, the T-DNA including the identification sequence and plant selectable marker and the T-DNA comprising the gene of interest may be found in separate bacterial cells or strains used together for transformation.

In still another embodiment, DNA sequences including the (i) gene of interest; and (ii) identification sequence expressed in seed and physically linked to a selectable or screenable marker gene may be introduced into a plant cell by a physical method such as microprojectile bombardment. In such an embodiment, the DNA sequences of (i) and (ii) can be located on separate DNA fragments that may be mixed together prior to or during the coating of microprojectiles with DNA. The DNA sequences may be present on a single microprojectile, or they may be present on separate microprojectiles that are mixed together prior to bombardment.

The phenotype conveyed by the identification sequence can be achieved by ectopic overexpression of a heterogenous or endogenous gene linked to a constitutive or seed-specific promoter, or by downregulation of an endogenous gene using antisense RNA, RNA interference or co-suppression technology. Examples of the endogenous gene may include, but are not limited to, genes involved in sugar/starch metabolism, protein metabolism, and fatty acid metabolism.

In one embodiment, seed expression of the identification sequence results in a detectable phenotype in seed of a transgenic plant containing an identification sequence. In some embodiments the phenotype may be detected by visual inspection, and may include a change in seed color, opacity (or translucence), fluorescence, texture, size, shape, germinability, viability, or generally any component or property that is physically or biochemically assayable and different from that found in the nontransgenic recipient genotype. In certain embodiments, the identification sequence includes a gusA, gfp (Pang et al., 1996), phytoene synthase, or phytoene desaturase encoding gene, or an anthocyanin gene (Pl, Lc, B-Peru, C1, R, Rc, mybA or myb1 (e.g. Selinger et al., 1998; Ludwig et al., 1989; Himi et al., 2005; Kobayashi et al., 2002)). In a particular embodiment, the identification gene comprises a crtB gene encoding a phytoene synthase (U.S. Pat. Nos. 5,429,939; 6,429,356; 5,545,816), including a gene comprising a crtB sequence codon-optimized for expression in a monocot plant, such a corn plant. Another example of gene that could be used in this regard is a gene involved in production of seed pigment.

In other embodiments, the phenotype is assayable by detection of a catalytic activity. In yet other embodiments, the phenotype is a tissue ablation phenotype, for instance a blockage in the formation of pollen, egg, or seed tissue. Compositions and methods that silence genes required for the production or viability of gametes, reducing or preventing fertilizations that include the marker gene, are also envisioned. For example, sequences could be used that result in the silencing of genes required for pollen development and viability. The pollen that are derived from meiotic segregants carrying the marker gene would not develop or would be inviable, thus preventing the transmission of the marker gene to the progeny through the pollen. In outcross pollinations, all progeny would be marker free. Use of sequences that result in silencing of other endogenous genes (e.g. RNAi technologies including miRNA) to result in a seed phenotype is also envisioned. Such genes include, but are not limited to: genes encoding or modifying expression of seed storage proteins such as zeins, Opaque2, Waxy, and other genes encoding proteins involved in carbohydrate, protein, and/or lipid accumulation in seeds.

Expression of an identification sequence that confers a phenotype of nonviable pollen is also desirable because only the pollen grains without the identification sequence will be capable of fertilizing eggs thus increasing the yield of seeds free of the identification sequence and the marker sequence when the transgenic line carrying the identification sequence under the control of a pollen-specific promoter is used as a male pollinator. The identification sequence can produce a protein that is lethal to the pollen or inhibitory to pollen germination. Alternatively, expression of a pair of inverted repeats homologous to an essential endogenous pollen gene can be used to silence the gene rendering the pollen nonviable. Examples of pollen specific genes and promoters are known to those skilled in the art and include for instance LAT52 and LAT59 genes and promoters of tomato as described (Eyal et al., 1995).

In another embodiment, the identification sequence can be expressed in both the seed and the pollen for further enhancing the selection of seeds with the gene of interest and eliminating the seeds with the identification sequence and the marker gene. This can be achieved by using an identification sequence comprised of two transgenes; the one of which expresses in the seed and the other expresses in the pollen. Alternatively, a promoter that can express the same identification sequence in the pollen and seed can also result in a detectable phenotype in both the pollen and the seed. Examples of promoters that express in pollen and seed are the promoters from the maize Waxy gene (zmGBS; Shure et al., 1983), and the rice small subunit ADP-glucose pyrophosphorylase gene (osAGP; Anderson et al., 1991). Pollen and seed expression patterns are also described in Russell and Fromm, 1997.

Figure 12:
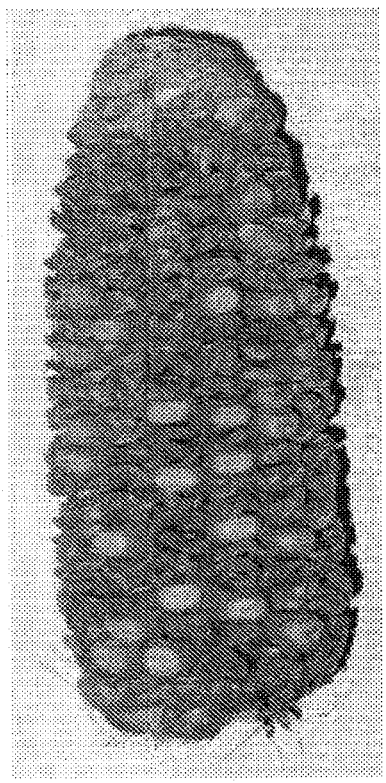
FIG. 12. Corn ear expressing seed-specific yeast ATP dependent phosphofructokinase abolished normal kernel development.

The identification sequence may alternatively alter carbohydrate, protein, lipid, or other products of cell or seed metabolism so as to yield a detectable phenotype. In one embodiment, the identification sequence allows for endosperm-specific expression of a sacB gene encoding a levansucrase or a yeast ATP-dependent phosphofructokinase (ATP-PFK) which abolishes starch accumulation in seeds containing the identification sequence and marker gene (Caimi et al., 1996; FIG. 12). The identification sequence can be a gene. The identification sequence can further encode a transcriptional or translational fusion (e.g. U.S. Pat. No. 6,307,123; U.S. Patent Publication 20060064772).

U.S. Pat. No. 6,307,123 relates to the construction of a translational fusion between a selectable marker gene (nptII) and a screenable marker gene (gfp). The method can be applied to produce a fusion between an identification sequence described herein and a selectable or a screenable marker described herein.

Another method that can be used to make a polypeptide fusion is based on the Ubiquitin (Ub) processing pathway. This method can be used to cleave a long polypeptide comprising two protein domains into two separate active proteins. In this method, a single gene cassette can encode two ORFs, where the two ORFs, e.g., for crtB and EPSPS-CP4 are separated by the 14 C-terminal amino acids of Ub, followed by a full-length Ub sequence. After translation in vivo, endogenous de-ubiquitinating enzymes (DUBs) cleaves the polyprotein into three separate units: 1) the N-terminal protein, which comprises the identification sequence crtB terminating in the 14 C-terminal amino acids of Ub; 2) a Ub monomer; and 3) the C-terminal polypeptide, which encodes a selectable marker EPSPS-CP4. Such methods are known to those skilled in the art (e.g. Walker et al, 2007).

A transcriptional fusion between an identification sequence and a selectable or a screenable marker can be made by using internal ribosome entry sites (IRES). For example, a transcript could be made that encodes the ORF of crtB followed by the ORF of ESPSP-CP4 with a functional IRES element positioned between them. Several IRES are known to those skilled in the art (see e.g., Dinkova et al. 2005 and references therein; and U.S. Pat. No. 7,119,187, incorporated herein by reference).

The phenotype of the identification sequence in seed tissue may also be detected by methods including visual, biochemical, immunological and nucleic-acid based (e.g. PCR-based) methods, among others. The identification sequence may confer a detectable phenotype in seed tissue that may be distinguished from the phenotype of the marker gene. The phenotype conferred by the identification sequence can include altered seed germination. The identification sequence may be expressed in one or more portions of a seed (kernel), including the embryo, endosperm, cotyledon(s), and seed coat (testa), such that a phenotype may be discerned.

The identification sequence may also cause a seedless phenotype. To accomplish tissue ablation, in one embodiment, the identification sequence directs ovule-specific expression of defH9-iaaM or rolB in plants (e.g. Rotino et al. 1997, Carmi et al. 2003, GenBank AM422760, X64255, AE009418), which abolishes ovule development and results in a seedless phenotype in marker and identification sequence-containing ovaries. In yet another embodiment, the identification sequence directs over expression of OsCDPK2 in cereal crops disrupting seed development (Morello et al. 2000; e.g., GenBank Y13658).

Genetic elements may also be designed to suppress the expression of an endogenous gene, resulting in the production of a seed phenotype that permits distinguishing of seeds that contain the marker gene from those that do not. The genetic elements of this identification sequence are physically linked to the marker gene, e.g. embedded within the marker DNA cassette, such that the seed phenotype is linked to the presence of the marker, allowing for the rapid identification of marker containing seeds.

RNAi may be used to silence one or more genes resulting in an easily scored, preferably visible, seed phenotype. The DNA sequences required for an RNAi-mediated seed phenotype are positioned on the same T-DNA as the marker gene. Any progeny seed that contains the marker gene would also display the seed phenotype and would be easily identified. Such seeds would not need to be grown and screened for the presence of the marker gene. Thus, only seeds without the phenotype conferred by the identification sequence are grown and/or screened for the presence of the GOI. Depending on whether the seeds are from self-pollination or outcrossing, this method reduces the number of seeds that need to be planted and screened by at least 3× for selfing plant species or 1× for outcrossing plant species.

A wide variety of compositions are known to those skilled in the art that can be used to silence a target gene using RNAi related pathways. One embodiment is to assemble a DNA cassette that will transcribe an inverted repeat of sequences, to produce a double-stranded RNA (dsRNA), typically at least about 19-21 bp in length and corresponding to a portion of one or more genes targeted for silencing. The dsRNA can be about 19-21 bp in length and corresponding to a portion of one or more genes targeted for silencing. This DNA cassette including an identification sequence is positioned within the same T-DNA as the selectable marker gene. Other methods to silence a gene known to those skilled in the art include, but are not limited to: cosuppression, antisense, expression of miRNAs (natural or engineered), expression of trans-acting siRNAs, and expression of ribozymes. Any of these methods may be used if the sequences required for the gene silencing effect are positioned in the same T-DNA as the marker gene.

The identification sequence may increase or decrease seed size. In one embodiment, the identification sequence confers down regulation of AP2 gene (e.g., GenBank U12546) by antisense RNA or RNA interference or cosuppression technology (Jofuku et al., 2005), which results in larger seeds containing the identification sequence and selectable marker genes. The larger seed size may also be achieved by ectopic expression of an AFR2 gene (Schruff et al., 2006; e.g., GenBank Accessions NM_203251; NM_180913), or ANT transcription factor (Mizukami and Fisher, 2000; e.g., GenBank NM_202701, NM_119937, NM_180024, NM_101474, NM_202110). In another embodiment, the identification sequence conveys down regulation of a LEC2 (e.g., GenBank AF400123) or a Snf-1 (GenBank AB101657, AB101656, AB101655) gene by antisense RNA or RNAi or cosuppression technology, which leads to decreased seed size (Mendoza et al., 2005; Radchuk et al., 2006). The changed seed size can be easily sorted by weight, shape or sieving by manual and/or mechanical means.

It is specifically contemplated that automated screening techniques may be implemented with the current invention for the identification of seeds having a particular detectable phenotype. In this manner large numbers of seeds can be efficiently screened and seeds lacking an identification sequence may be collected. Automated techniques may be faster, less expensive and more accurate than reliance upon human technicians. Such seed sorting machines which could be used in this manner have been described. For example, U.S. Pat. No. 4,946,046 describes an apparatus for sorting seeds according to color. In this machine, seeds are sorted according to color by placing the seeds in uniform rows of indentations in a rotating drum and passing the seeds beneath a digital imaging camera and a light source. Images are read by the camera and are fed to a computer, which also receives information from a drum speed sensor. The computer generates a signal which causes a blast of air to blow through an opening in the bottom of an indentation containing a colored seed to collect such seed. Collected seeds are fed into a collection hopper, and the non-colored seeds into a separate hopper.

By varying the wavelength of the light source used for detection of colored seeds, as well as barrier filters placed between the colored seed and the detection camera, potentially any identification marker could be detected with this technique. For example, to detect seeds expressing GFP, the excitation wavelength is in the blue light UV spectrum, typically at about 395 nm. Suitable light sources for UV emission are well known to those of skill in the art, and include xenon or mercury lamps. Suitable filter sets also are well known to those of skill in the art, and include, for example, a BP450-490 exciter filter, an FT510 chromatic beam splitter, and a BP515-565 barrier filter (Carl Zeiss, Inc., Thornwood, N.Y.). Such filter sets and emission wavelengths are discussed in more detail in Heim and Tsien, 1996, the disclosure of which is specifically incorporated herein by reference in its entirety.

By use of constructs including one or more identification sequence(s), the selective power can be extended to multiple selectable and/or screenable genes and genes of interest. Therefore, large numbers of transgenic seeds, representing a variety of different transformation events, can be efficiently screened and only those seeds having (or lacking) a desired set of identification sequences may be selected.

A recombinant DNA vector may, for example, be a linear DNA segment or a closed circular plasmid. The vector system may be a single vector or plasmid or two or more vectors or plasmids that together contain the total DNA to be introduced into the plant genome. Nucleic acid molecules as set forth herein can, for example, be suitably inserted into a vector under the control of a suitable promoter that functions in a plant cell to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function and the particular vector and plant cell with which it is used or is compatible.

A number of vectors suitable for stable transformation of plant cells or for the establishment of transgenic plants are well known, e.g., Gelvin et al. (1990). Typically, plant expression vectors include, but are not limited to, one or more gene of interest transcription units, each of which includes: a 5' untranslated region, which includes sequences that control transcription (e.g., cis-acting promoter sequences such as enhancers, the transcription initiation start site, etc.) and translation (e.g., a ribosome binding site) of an operably linked protein-coding sequence ("open reading frame", ORF); a 3' untranslated region that includes additional regulatory regions from the 3' end of plant genes (Thornburg et al., 1987); An et al., 1989), e.g., a 3' terminator region to increase mRNA stability. Alternatively a plant expression vector may be designed for expression of an mRNA molecule that may, for instance, alter plant gene expression by an RNAi-mediated approach. In addition, such constructs commonly include a selectable and/or screenable marker transcription unit and optionally an origin of replication or other sequences required for replication of the vector in a bacterial host cell.

The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, LBA4404, EHA101, or EHA105 carrying a plasmid having a transfer function for the expression unit. Other strains known to those skilled in the art of plant transformation can function in the present invention.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes. These 3' untranslated regions contain mRNA transcription termination signals. Other movable elements contained in plant expression vectors may include 5' leader sequences, transit signal sequences, and coding sequences.

Expression and cloning vectors may contain a selection gene, also referred to as a plant selectable marker. This gene encodes a protein necessary for the survival or growth of transformed plant cells grown in a selective culture regimen. Typical selection genes encode proteins that confer resistance to selective agents such as antibiotics including herbicides, or other toxins, e.g., neomycin, methotrexate, dicamba, glufosinate, or glyphosate. Those cells that are successfully transformed with a heterologous protein or fragment thereof produce a protein conferring, e.g. drug resistance and thus survive the selection regimen. Examples of various selectable/screenable/scorable markers and genes encoding them are disclosed in Miki and McHugh, 2004.

An expression vector for producing a mRNA can also contain an inducible or tissue specific promoter that is recognized in the host plant cell and is operably linked to the nucleic acid encoding, the nucleic acid molecule, or fragment thereof, of interest. Plant promoters are discussed below.

In one embodiment, the plant transformation vector that is utilized includes an isolated and purified DNA molecule including a heterologous seed-specific promoter operatively linked to one or more nucleotide sequences of the present invention. In another embodiment, the promoter is seed-expressed, but not seed-specific. A plant transformation vector may contain sequences from one or more genes, thus allowing production of more than mRNA in a plant cell. One skilled in the art will readily appreciate that segments of DNA can be combined into a single composite DNA segment for expression in a transgenic plant.

Suitable methods for transformation of host cells for use with the current invention are believed to include virtually any method by which DNA can be introduced into a cell (see, for example, Miki et al., 1993), such as by transformation of protoplasts (U.S. Pat. No. 5,508,184; Omirulleh et al., 1993), by desiccation/inhibition-mediated DNA uptake (Potrykus et al., 1985), by electroporation (U.S. Pat. No. 5,384,253), by agitation with silicon carbide fibers (Kaeppler et al., 1990; U.S. Pat. Nos. 5,302,523; and 5,464,765), by *Agrobacterium*-mediated transformation (U.S. Pat. Nos. 5,563,055; 5,591,616; 5,693,512; 5,824,877; 5,981,840; 6,384,301) and by acceleration of DNA coated particles (U.S. Pat. Nos. 5,015,580; 5,550,318; 5,538,880; 6,160,208; 6,399,861; 6,403,865; Padgette et al. 1995), etc. Through the application of techniques such as these, the cells of virtually any species may be stably transformed. In the case of multicellular species, the transgenic cells may be regenerated into transgenic organisms.

The most widely utilized method for introducing an expression vector into plants is based on the natural transformation system of *Agrobacterium* (for example, Horsch et al., 1985) The Ti and Ri plasmids of *A. tumefaciens* and *A. rhizogenes*, respectively, carry genes responsible for genetic transformation of the plant. Descriptions of *Agrobacterium* vector systems and methods for *Agrobacterium*-mediated gene transfer are provided by numerous references, including Gruber et al., 1993; Miki et al., 1993, Moloney et al., 1989, and U.S. Pat. Nos. 4,940,838 and 5,464,763. Other bacteria such as *Sinorhizobium*, *Rhizobium*, and *Mesorhizobium* that interact with plants naturally can be modified to mediate gene transfer to a number of diverse plants (Broothaerts et al., 2005). These plant-associated symbiotic bacteria can be made competent for gene transfer by acquisition of both a disarmed Ti plasmid and a suitable binary vector. DNA sequences to be transferred via an *Agrobacterium*-mediated transformation method include one or more "border" sequences, such as right border (RB) and left border (LB) sequences that usually define the extent of the transferred DNA (T-DNA) containing one or more genes to be expressed in a plant cell, and may further include an enhancer sequence such as an overdrive sequence (Toro et al., 1989) or a plurality of overdrive sequences as disclosed in U.S. Provisional Patent Application No. 60/831,814, incorporated herein by reference.

Techniques that may be particularly useful in the context of cotton transformation are disclosed in U.S. Pat. Nos. 5,846,797, 5,159,135, 5,004,863, and 6,624,344. Techniques for transforming *Brassica* plants in particular are disclosed, for example, in U.S. Pat. No. 5,750,871; and techniques for transforming soybean are disclosed in, for example, Zhang et al., 1999, U.S. Pat. Nos. 6,384,301, and 7,002,058. Techniques for transforming corn are disclosed in WO9506722. Some non-limiting examples of plants that may find use with the invention include alfalfa, barley, beans, beet, broccoli, cabbage, carrot, canola, cauliflower, celery, Chinese cabbage, corn, cotton, cucumber, dry bean, eggplant, fennel, garden beans, gourd, leek, lettuce, melon, oat, okra, onion, pea, pepper, pumpkin, peanut, potato, pumpkin, radish, rice, sorghum, soybean, spinach, squash, sweet corn, sugarbeet, sunflower, tomato, watermelon, and wheat.

A vector or construct may also include various regulatory elements. The 5' non-translated leader sequence can be derived from the promoter selected to express the heterologous gene sequence of the DNA molecule of the present invention, and can be specifically modified if desired so as to increase translation of mRNA. The 5' non-translated regions can also be obtained from plant viral RNAs (e.g. Tobacco mosaic virus, Tobacco etch virus, Maize dwarf mosaic virus, Alfalfa mosaic virus) from suitable eukaryotic genes, plant genes (wheat and maize chlorophyll a/b binding protein gene leader), or from a synthetic gene sequence. The leader sequence could also be derived from an unrelated promoter or coding sequence. Leader sequences useful in context of the present invention include the maize Hsp70 leader (U.S. Pat. Nos. 5,362,865 and 5,859,347, herein incorporated by reference in their entirety), and the TMV omega element (Gallie et al., 1989). Examples of translation leader sequences include maize and *Petunia* heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362,865), AtAnt1, TEV (Carrington and Freed, 1990), AGRtunos (GenBank Accession V00087; Bevan et al., 1983), OsAct1 (U.S. Pat. No. 5,641,876), OsTPI (U.S. Pat. No. 7,132,528), and OsAct15 (US Publication No. 20060162010), among others.

Intron sequences are known in the art to aid in the expression of transgenes in monocot plant cells. Examples of introns include the corn actin intron (U.S. Pat. No. 5,641,876), the corn HSP70 intron (ZmHSP70; U.S. Pat. Nos. 5,859,347; 5,424,412), and rice TPI intron (OsTPI; U.S. Pat. No. 7,132,528), and are of benefit in practicing this invention.

A vector may also include a transit peptide nucleic acid sequence. Many chloroplast-localized proteins, including those involved in carotenoid synthesis, are expressed from nuclear genes as precursors and are targeted to the chloroplast by a chloroplast transit peptide (CTP) that is removed after the import steps. Examples of other such chloroplast proteins include the small subunit (SSU) of Ribulose-1,5-bisphosphate carboxylase, and the light-harvesting complex protein I and protein II. It has been demonstrated in vivo and in vitro that non-chloroplast proteins may be targeted to the chloroplast by use of protein fusions with a CTP and that a CTP sequence is sufficient to target a protein to the chloroplast. Incorporation of a suitable chloroplast transit peptide, such as the *Arabidopsis thaliana* (At) EPSPS CTP (Klee et al., 1987), and the *Petunia hybrida* (Ph.) EPSPS CTP (della-Cioppa et al., 1986) has been shown to target heterologous protein sequences to chloroplasts in transgenic plants. Those skilled in the art will recognize that various chimeric constructs can be made, if needed, that utilize the functionality of a particular CTP to import a given gene product into a chloroplast. Other CTPs that may be useful in practicing the present invention include PsRbcS-derived CTPs (*Pisum sativum* Rubisco small subunit CTP; Coruzzi et al., 1984); AtRbcS CTP (*Arabidopsis thaliana* Rubisco small subunit 1A CTP; CTP1; U.S. Pat. No. 5,728,925); AtShkG CTP (CTP2; Klee et al., 1987); AtShkGZm CTP (CTP2 synthetic; codon optimized for monocot expression;

SEQ ID NO:14 of WO04009761); PhShkG CTP (*Petunia hybrida* EPSPS; CTP4; codon optimized for monocot expression; Gasser et al., 1988); TaWaxy CTP (*Triticum aestivum* granule-bound starch synthase CTPsynthetic, codon optimized for corn expression: Clark et al., 1991): OsWaxy CTP (*Oryza sativa* starch synthase CTP; Okagaki, 1992); NtRbcS CTP (*Nicotiana tabacum* ribulose 1,5-bisphosphate carboxylase small subunit chloroplast transit peptide; Mazur, et al., 1985); ZmAS CTP (*Zea mays* anthranilate synthase alpha 2 subunit gene CTP; Gardiner et al., 2004); and RgAS CTP (*Ruta graveolens* anthranilate synthase CTP; Bohlmann, et al., 1995). Other transit peptides that may be useful include maize cab-m7 signal sequence (PCT WO 97/41228) and the pea (*Pisum sativum*) glutathione reductase signal sequence (PCT WO 97/41228).

Termination of transcription may be accomplished by a 3' non-translated DNA sequence operably linked to a recombinant transgene (e.g. the gene of interest, the identification sequence including a screenable gene, or the plant selectable marker gene). The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region (Fraley et al., 1983), is commonly used in this capacity. Polyadenylation molecules from a *Pisum sativum* RbcS2 gene (Ps.RbcS2-E9; Coruzzi et al., 1984), AGRtu.nos (Genbank Accession E01312), E6 (Accession #U30508), rice glutelin (Okita et al., 1989), and TaHsp17 (wheat low molecular weight heat shock protein gene; Accession #X13431) in particular may be of benefit for use with the invention.

For embodiments of the invention in which the use of a constitutive promoter is desirable, any well-known constitutive plant promoter may be used. Constitutive plant promoters include, for example, the cauliflower mosaic virus (CaMV) 35S promoter, which confers constitutive, high-level expression in most plant tissues (see, e.g., Odell et al., 1985), including monocots (see, e.g., Dekeyser et al., 1990); Terada et al., 1990); the nopaline synthase promoter (An et al., 1988), the octopine synthase promoter (Fromm et al., 1989), cauliflower mosaic virus 19S promoter, figwort mosaic virus 35S promoter, rice actin 1 promoter, mannopine synthase promoter, and a histone promoter.

For other embodiments of the invention, well-known plant gene promoters that are regulated in response to environmental, hormonal, chemical, and/or developmental signals may be used, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, etc. It may also be advantageous to employ (6) organ-specific promoters (e.g., Roshal et al., 1987; Schernthaner et al., 1988; Bustos et al., 1989).

There are a wide variety of plant promoter sequences which may be used to drive tissue-specific expression of polynucleotides in transgenic plants. Indeed, in particular embodiments of the invention, the promoter used is a seed specific promoter. The promoter for β-conglycinin (Chen et al., 1989) or other seed-specific promoters such as the napin promoter, which are regulated during plant seed maturation (Kridl et al., 1991; Kohno-Murase et al., 1994), barley Hv.Per1 (Stacey et al., 1996), phaseolin (Bustos et al., 1989), soybean trypsin inhibitor (Riggs et al., 1989), ACP (Baerson et al., 1993), stearoyl-ACP desaturase (Slocombe et al., 1994), soybean α' subunit of β-conglycinin (P-Gm7S, see for example, Chen et al., 1986), *Vicia faba* USP (P-Vf.Usp, see for example, SEQ ID NO: 1, 2, and 3, U.S. Appln. Pub. 20030229918), the globulin promoter (see for example Belanger and Kriz, 1991), soybean alpha subunit of β-conglycinin (7S alpha; U.S. Pat. No. 6,825,398, incorporated by reference) and *Zea mays* L3 oleosin promoter (P-Zm.L3, see, for example, Hong et al., 1997; see also U.S. Pat. No. 6,433,252, the disclosure of which is specifically incorporated herein by reference).

The zeins are a group of storage proteins found in *Zea mays* endosperm. Genomic clones for zein genes have been isolated (Pedersen et al., 1982; U.S. Pat. No. 6,326,527), and the promoters from these clones, including the 15 kDa, 16 kDa, 19 kDa, 22 kD, 27 kDa, and gamma genes, could also be used. Other promoters known to function, for example, in *Zea mays* include the promoters for the following genes: waxy (Russell and Fromm, 1997; Shure et al., 1983), Brittle (Giroux et al., 1994), Shrunken 2, Branching enzymes I and II, starch synthases, debranching enzymes, oleosins, glutelins, and sucrose synthases. Another promoter for *Zea mays* endosperm expression is the promoter for the glutelin gene from rice, more particularly the Osgt-1 promoter (Zheng et al., 1993). Examples of such promoters in rice include those promoters for the ADPGPP subunits, the granule bound and other starch synthase, the branching enzymes, the debranching enzymes, sucrose synthases (Yang et al., 1990), and Betl1 (basal endosperm transfer layer) and globulin1.

Examples of other promoters that may be useful with the present invention are described in the U.S. Pat. No. 6,437,217 (maize RS81 promoter), U.S. Pat. No. 5,641,876 (rice actin promoter; OsAct1), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. Pat. No. 7,151,204 (maize chloroplast aldolase promoter). Additional promoters that may find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., 1987), the CaMV 35S promoter (Odell et al., 1985), the figwort mosaic virus 35S-promoter (Walker et al., 1987), the sucrose synthase promoter (Yang et al., 1990), the R gene complex promoter (Chandler et al., 1989), and the chlorophyll a/b binding protein gene promoter, etc. In the present invention, CaMV35S with enhancer sequences (e35S; U.S. Pat. Nos. 5,322,938; 5,352,605; 5,359,142; and 5,530,196), FMV35S (U.S. Pat. Nos. 6,051,753; 5,378,619), peanut chlorotic streak caulimovirus (PC1SV; U.S. Pat. No. 5,850,019), At.Act 7 (Accession #U27811), At.ANT1 (US Patent Application Publication 20060236420), FMV.35S-EF1a (U.S. Patent Application Publication 20050022261), eIF4A10 (Accession #X79008) and AGRtu.nos (GenBank Accession V00087; Depicker et al, 1982; Bevan et al., 1983), rice cytosolic triose phosphate isomerase (OsTPI; U.S. Pat. No.

7,132,528), and rice actin 15 gene (OsAct15; U.S. Patent Application Publication 20060162010) promoters may be of particular benefit. In some instances, e.g., OsTPI and OsAct 15, a promoter may include a 5'UTR and/or a first intron. Other promoters useful in the practice of the invention that are known by one of skill in the art are also contemplated by the invention.

A plant expression vector may also include a screenable or scorable marker gene cassette that may be used in the present invention to monitor segregating cells or progeny for (loss of) expression. Exemplary markers are known and include β-glucuronidase (GUS) that encodes an enzyme for various chromogenic substrates (Jefferson et al., 1987a; Jefferson et al., 1987b); an R-locus gene, that encodes a product that regulates the production of anthocyanin pigments (red color) in plant tissues (Dellaporta et al., 1988); a β-lactamase gene (Sutcliffe et al., 1978); a gene that encodes an enzyme for that various chromogenic substrates are known (e.g., PADAC, a chromogenic cephalosporin); a luciferase gene (Ow et al., 1986); a xylE gene (Zukowsky et al., 1983) that encodes a catechol dioxygenase that can convert chromogenic catechols; an α-amylase gene (Ikatu et al., 1990); a tyrosinase gene (Katz et al., 1983) that encodes an enzyme capable of oxidizing tyrosine to DOPA and dopaquinone that in turn condenses to melanin; green fluorescence protein (Elliot et al., 1999) and an α-galactosidase. A screenable or scorable marker gene may encode the same gene product as an identification sequence including a screenable or scorable gene, or a different gene product. However, the identification sequence is expressed in egg, pollen or seed tissues, while the screenable or scorable marker gene is expressed during the process of identifying transformed plant cells. The identification sequence may also be expressed constitutively, but only convey a phenotype in egg, pollen, or seed tissues.

Transgenic plants may be regenerated from a transformed plant cell by methods well known in the field of plant cell culture. A transgenic plant formed using Agrobacterium transformation methods typically contains a single simple recombinant DNA sequence inserted into one chromosome and is referred to as a transgenic event. Such transgenic plants can be referred to as being heterozygous for the inserted exogenous sequence. A transgenic plant homozygous with respect to a transgene can be obtained by sexually mating (selfing) an independent segregant transgenic plant that contains a single exogenous gene sequence to itself, for example an F0 plant, to produce F1 seed. One fourth of the F1 seed produced will be homozygous with respect to the transgene. Germinating F1 seed results in plants that can be tested for zygosity, typically using a SNP assay or a thermal amplification assay that allows for the distinction between heterozygotes and homozygotes (i.e., a zygosity assay).

A number of identification sequences may be used, for instance genes whose expression may result in a visible phenotype, including use of gus, gfp, and luc (see, e.g., Ow et al., 1986; WO 97/41228 and U.S. Pat. No. 6,583,338; e.g., M26194; M15077). A levansucrase gene, sacB (Caimi et al., 1996; e.g., X02730) leading to a "shrunken" seed phenotype, or a pyrophosphatase gene (Hajirezaei et al., 1999) leading to inhibition of germination, may also be employed. Genes encoding phytoene synthase (crtB) are known in the art, including those from *Erwinia uredovora* (e.g. Misawa et al., 1990; Sandmann and Misawa, 1992; U.S. Pat. Nos. 5,429,939; 6,429,356), and *Pantoea/Enterobacter agglomerans* (e.g. GenBank M38423; M87280), among others. Seed-specific expression of crtB that results in orange coloration has been described (Shewmaker et al., 1999; U.S. Pat. No. 6,429,356).

Most transgenes producing pleiotropic seed phenotypes may be used as a visible label gene linked to a selectable marker to identify marker-free gene of interest positive seeds. The visible phenotype may be produced by ectopic overexpression of a transgene or result from down regulation of endogenous metabolic pathway genes by antisense RNA, RNA interference or co-suppression technology.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al. (1991); and Lewin (1994). The nomenclature for DNA bases as set forth at 37 CFR § 1.822 is used.

"CP4", "aroA:CP4", "AGRTU.aroA:CP4", "CP4 EPSPS" and "EPSPS CP4" refer to the EPSP synthase gene or protein purified from *Agrobacterium tumefaciens* (AGRTU) strain CP4 that when expressed in plants confers tolerance to glyphosate and glyphosate containing herbicide formulations (U.S. Pat. No. 5,633,435, herein incorporated by reference in its entirety). The gene sequence may be native or modified for enhanced expression in plants.

A DNA "segment" refers to a region of DNA sequence of a DNA construct. A DNA segment may be within, between, or flanking the T-DNA molecules found in a construct used for *Agrobacterium*-mediated plant cell transformation. For instance, a DNA segment may contain genetic elements for replication of plasmids in bacteria or other various elements and expression cassettes of the DNA construct designed for use in plant cell transformation. Thus, a "DNA cassette" may comprise a DNA segment, including element(s) for expression of the DNA sequence in a cell.

A "fusion protein" refers to a translational fusion expressed as a single unit, yet producing a gene product conferring the phenotypes of the protein encoded by the non-fused starting gene sequences.

An "isolated" nucleic acid is substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

The term "glyphosate resistance gene" refers to any gene that, when expressed as a transgene in a plant, confers the ability to tolerate levels of the herbicide glyphosate that would otherwise damage or kill the plant. Any glyphosate tolerance gene known to the skilled individual are suitable for use in the practice of the present invention. Glyphosate (including any herbicidally active form of N-phosphonomethylglycine and any salt thereof) inhibits the enzyme 5-enolpyruvylshikimate-3-phosphate synthase (EPSPS). A variety of native and variant EPSPS enzymes have been expressed in transgenic plants in order to confer glyphosate tolerance, any of which can be used in the invention. Examples of some of these EPSPSs include those described and/or isolated in accordance with U.S. Pat. Nos. 4,940,835, 4,971,908, 5,145,783, 5,188,642, 5,310,667, and 6,803,501. They can also be derived from a structurally distinct class of non-homologous EPSPS genes, such as the class II EPSPS genes isolated from *Agrobacterium* sp. strain CP4 (AGRTU.aroA:CP4).

The term "identification sequence" refers to a nucleic acid that encodes a product conferring a detectable phenotype such as a change in seed or gamete color, opacity or translucence, fluorescence, texture, size, shape, germinability, or viability, or other product of cell or seed metabolism. The identification sequence may include a nucleotide sequence (e.g. a gene fragment) that may confer a phenotype via down regulation of the expression of another gene, such as via an RNAi-mediated process. In certain embodiments, the identification sequence includes a screenable gene such as a gusA, gfp, or crtB gene. In a particular embodiment, the identification sequence includes a crtB gene encoding a phytoene synthase from *Erwinia herbicola* (*Pantoea agglomerans*; GenBank M38423, incorporated herein by reference; and U.S. Pat. Nos. 5,429,939, 6,429,356). The identification sequence is physically linked to a plant selectable, screenable, and/or scorable marker gene, such as one encoding antibiotic resistance or herbicide tolerance. The identification sequence can confer a detectable (e.g. screenable or selectable) phenotype in seed.

A first nucleic-acid sequence is "operably" connected or "linked" with a second nucleic acid sequence when the first nucleic acid sequence is placed in a functional relationship with the second nucleic acid sequence. For instance, a promoter is operably linked to a protein-coding sequence if the promoter affects the transcription or expression of the coding sequence. Generally, operably linked DNA sequences are contiguous and, where necessary to join two protein-coding regions, are in the same reading frame.

The term "plant" encompasses any higher plant and progeny thereof, including monocots (e.g., lily, corn, rice, wheat, barley, etc.), dicots (e.g., soybean, cotton, tomato, canola, potato, *Arabidopsis*, tobacco, etc.), gymnosperms (pines, firs, cedars, etc.) and includes parts of plants, including reproductive units of a plant (e.g., seeds, bulbs, tubers, or other parts or tissues from that the plant can be reproduced), fruit, flowers, etc.

A "recombinant" nucleic acid is made by an artificial combination of two otherwise separated segments of sequence, e.g., by chemical synthesis or by the manipulation of isolated segments of nucleic acids by genetic engineering techniques.

The terms "DNA construct" or "DNA vector" refers to any plasmid, cosmid, virus, autonomously replicating sequence, phage, or other circular single-stranded or double-stranded DNA or RNA derived from any source that includes one or more DNA sequences, such as promoters, protein-coding sequences, 3' untranslated regions, etc., that have been linked in a functionally operative manner by recombinant DNA techniques. Recombinant DNA vectors for plant transformation are commonly double-stranded circular plasmids capable of replication in a bacterial cell. Conventional compositions and methods for making and using recombinant nucleic acid constructs are well known, e.g. Sambrook et al., 1989; and Ausubel et al., 1992 (with periodic updates), and Clark et al. (1997), among others.

The term "promoter" or "promoter region" refers to a nucleic acid sequence, usually found upstream (5') to a coding sequence that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. A promoter region is responsible for driving the transcription of coding sequences under their control when introduced into a host as part of a suitable recombinant vector, as demonstrated by its ability to produce mRNA.

"Regeneration" refers to the process of growing a plant from a plant cell (e.g., plant protoplast or explant).

"Selectable marker" refers to a nucleic acid sequence whose expression confers a phenotype facilitating identification of cells containing the nucleic acid sequence. Selectable markers include those that confer resistance to toxic chemicals (e.g. antibiotic resistance), or impart a visually distinguishing characteristic (e.g. color changes or fluorescence).

Useful dominant plant selectable marker genes include genes encoding antibiotic resistance genes (e.g. resistance to hygromycin, imidazolinone, kanamycin, bleomycin, G418, streptomycin or spectinomycin); and herbicide resistance genes (e.g. phosphinothricin acetyltransferase, modified ALS, BAR, modified class I EPSPSs, class II EPSPSs, DMOs), among others.

Included within the terms "scorable marker genes" or "screenable marker genes" are genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g. α-amylase, β-lactamase, phosphinothricin acetyltransferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

"T-DNA" refers to a DNA molecule that integrates into a plant genome via an *Agrobacterium* or other *Rhizobia*-mediated transformation method. At least one end of the T-DNA molecule is flanked by at least one border region of the T-DNA from an *Agrobacterium* Ti or Ri plasmid. These border regions are generally referred to as the Right border (RB) and Left border (LB) regions and exist as variations in nucleotide sequence and length depending on their source (e.g. nopaline or octopine producing strains of *Agrobacterium*). The border regions commonly used in DNA constructs designed for transferring transgenes into plants are often several hundred polynucleotides in length and include a nick site where virD2 endonuclease derived from Ti or Ri helper plasmid digests the DNA and covalently attaches to the 5' end after T-strand formation to guide the T-strand integration into the genome of a plant. The T-DNA molecule(s) generally contain one or more plant expression cassettes.

The term "transgene" refers to any nucleic acid sequence nonnative to a cell or organism transformed into said cell or organism. "Transgene" may also refer to any endogenous sequence which is ectopically expressed by modifying coding sequence or regulatory sequences. "Transgene" also encompasses the component parts of a native plant gene modified by insertion of a nonnative or native nucleic acid sequence by directed recombination.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Figure 1A:
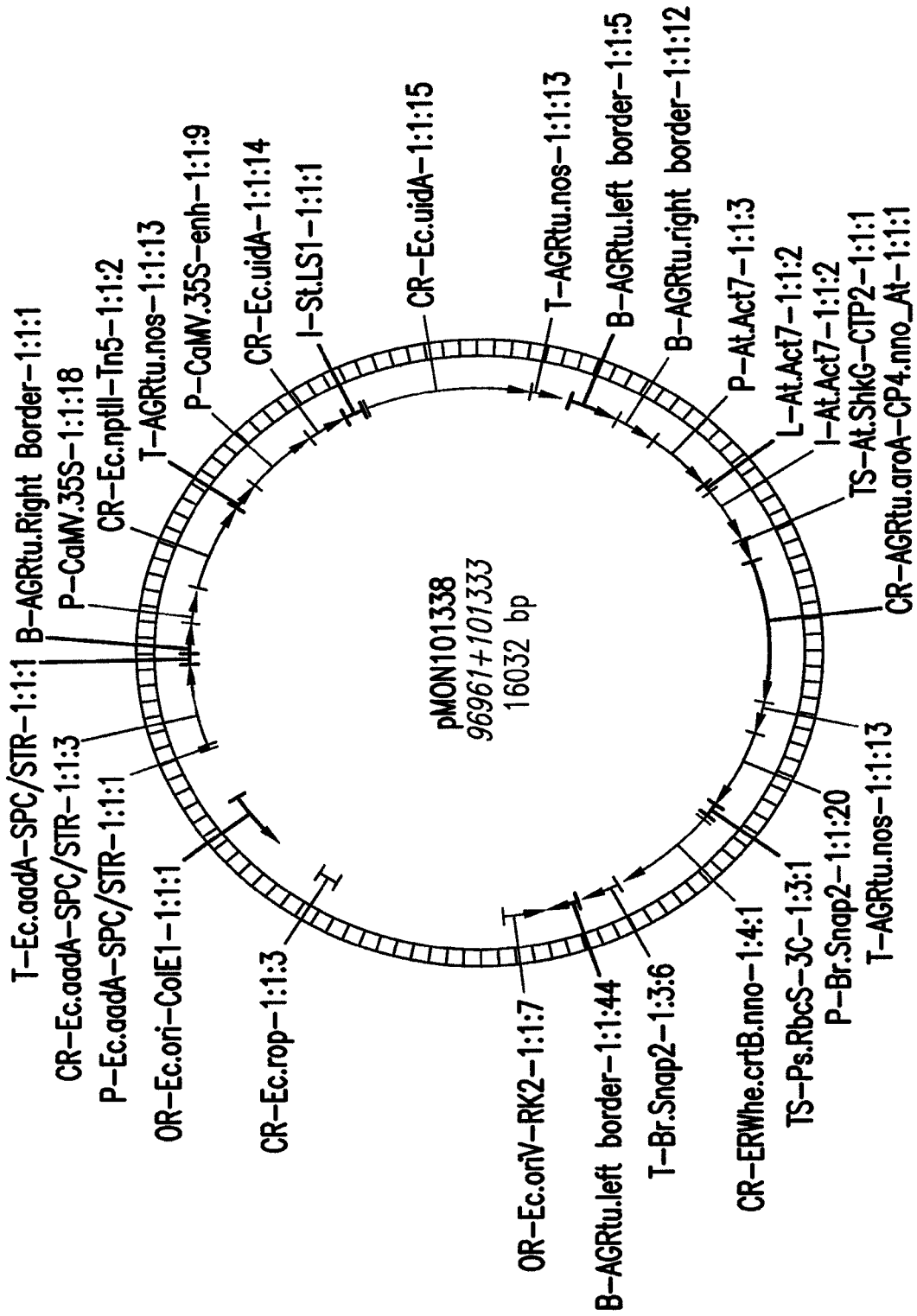
FIGS. 1A-1C. Schematic diagrams of: (A) pMON10338; (B) pMON10339; and (C) pMON67465.
Figure 1B:
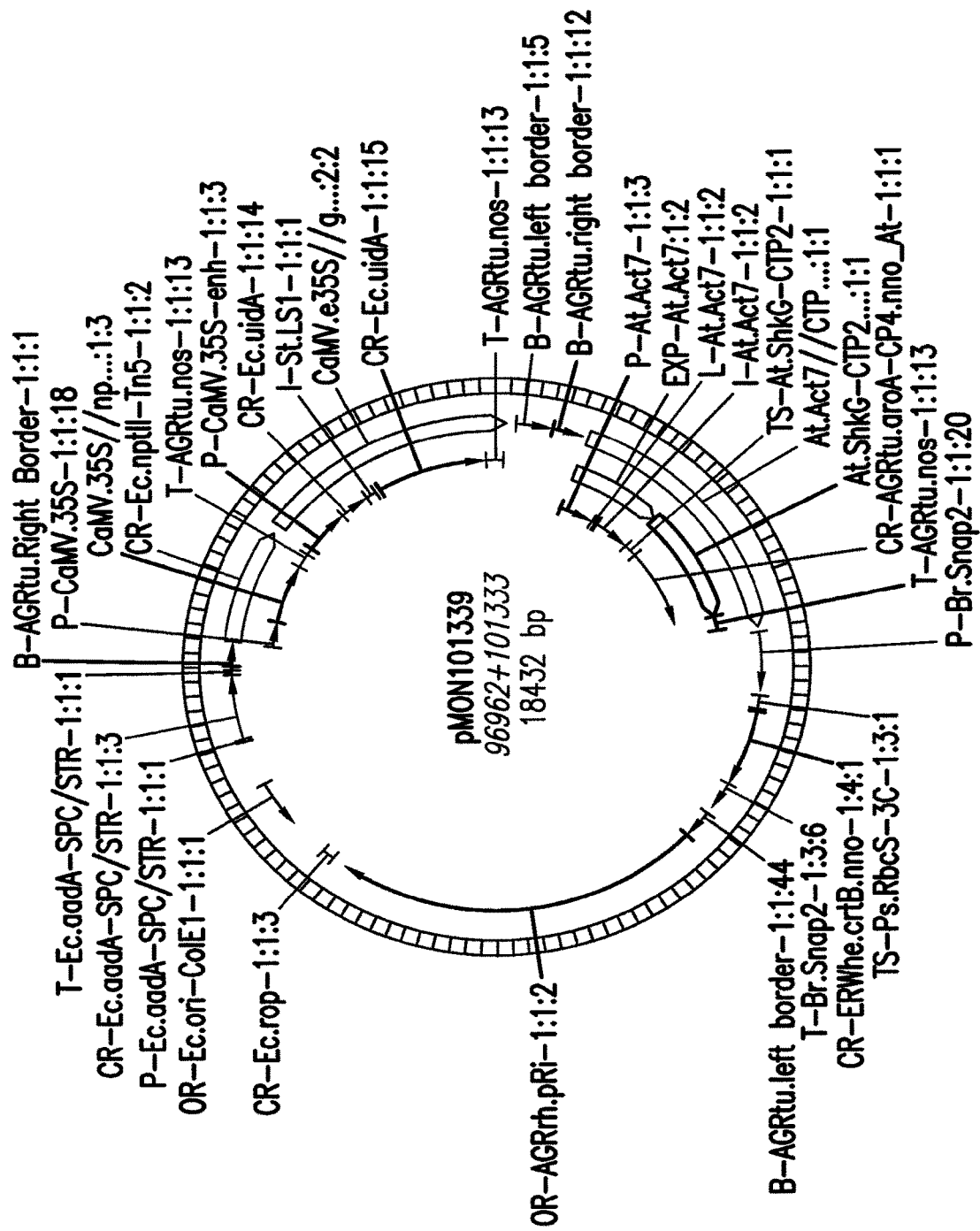
Figure 1C:
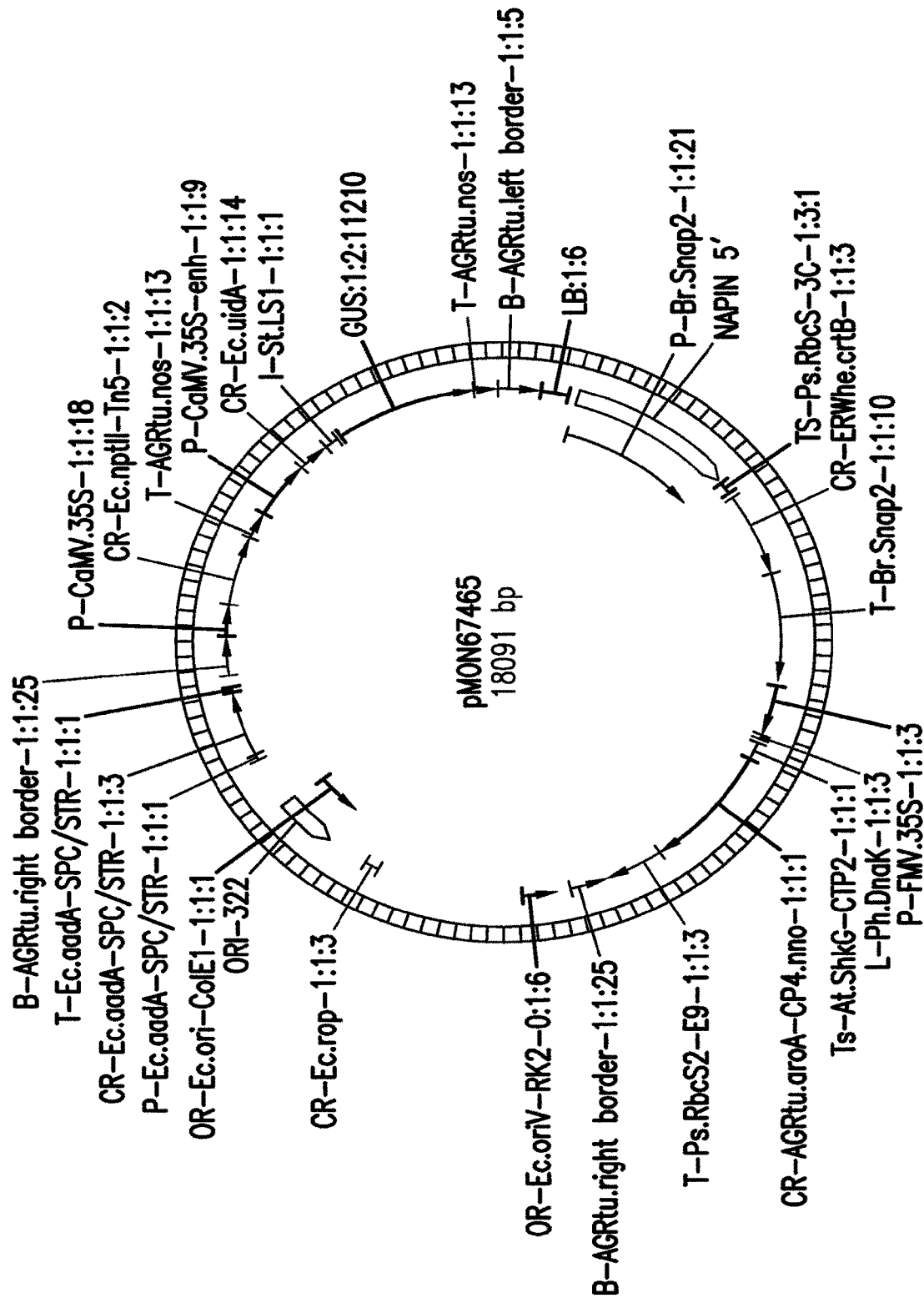
Figure 3:
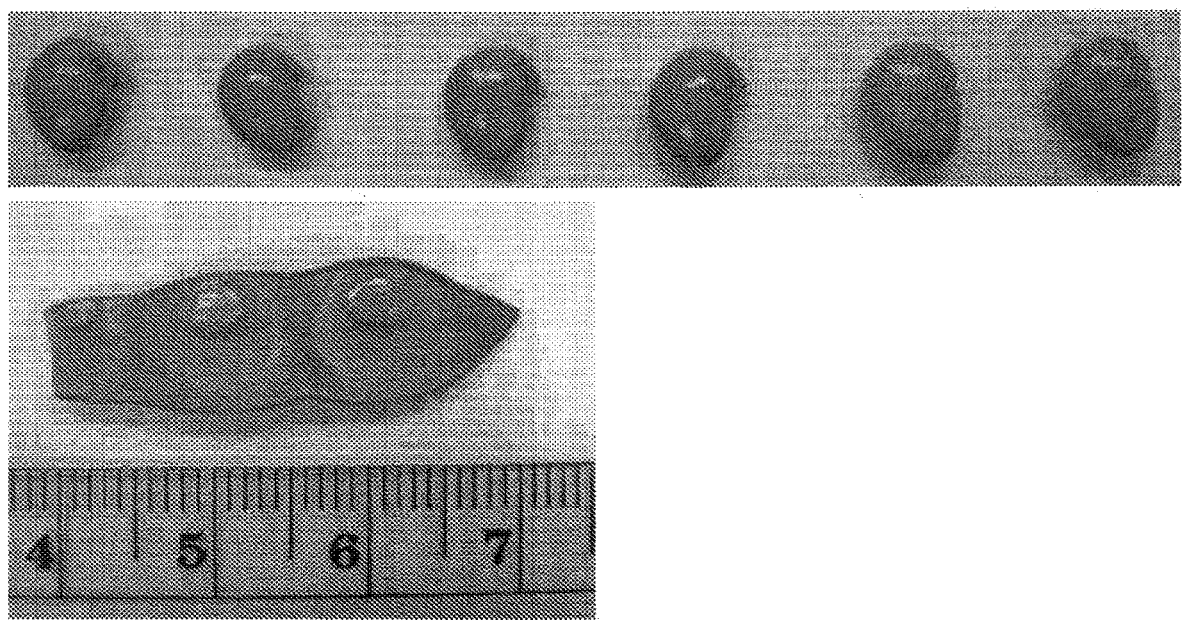
FIG. 3. CrtB expression in seed from event A33908.

Preparation of 2T-DNA Vectors with an Identification Sequence and Marker Gene, and a Gene-Of-Interest Two T-DNA plant expression vectors, pMON67465, pMON101338 and pMON101339 (FIG. 1), were constructed according to standard molecular cloning procedure (Sambrook et al., 1989). One T-DNA includes a CaMV 35S promoter operably linked to an nptII gene encoding resistance to kanamycin and a CaMV 35S promoter operably linked to a GUS reporter gene. The other T-DNA comprises a napin:ctp-crtB: napin 3' cassette and a 35S:ctp:CP4 EPSPS cassette, that confers glyphosate resistance. The crtB in pMON67465 with oriV replication origin was driven by a 1.8 kb seed-specific napin promoter and 1 kb napin terminator from Brassica napus. The crtB in pMON101338 with oriV replicon and in pMON101339 with pRi replication origin was driven by a shorter version of napin promoter (1 kb) and terminator (0.3 kb). The crtB gene, encoding a phytoene synthase from Erwinia sp. confers orange color to soybean seed without affecting transformation frequency (FIG. 3).

Example 2

Transformation and Regeneration of Soy Explants with pMON67465

Soybean (cv. A3244) tissues were transformed with pMON67465 (FIG. 1) via an Agrobacterium-mediated method, essentially as previously described (U.S. Pat. No. 6,384,301, herein incorporated by reference). Briefly, hand excised soy meristem explants were co-cultivated with Agrobacterium for 2-4 days at 23° C., transferred onto WPM solid medium with 75 μM glyphosate selection in a PLANT-CON and cultured at 28° C. under 16/8 light/dark period. After two weeks, the explants were transferred to fresh WPM medium and cultured until shoot harvest. After 2 months, shoots with true trifolia were cut and cultured onto BRM rooting medium for 2-4 weeks. The rooted plantlets were grown in greenhouse for seed maturation. Among 40 events analyzed, 72.5% displayed co-transformation with both T-DNAs. 45% of the 40 events contained both nptII and gus genes. Event A33908, containing T-DNAs from pMON67465, was further analyzed.

Figure 7:
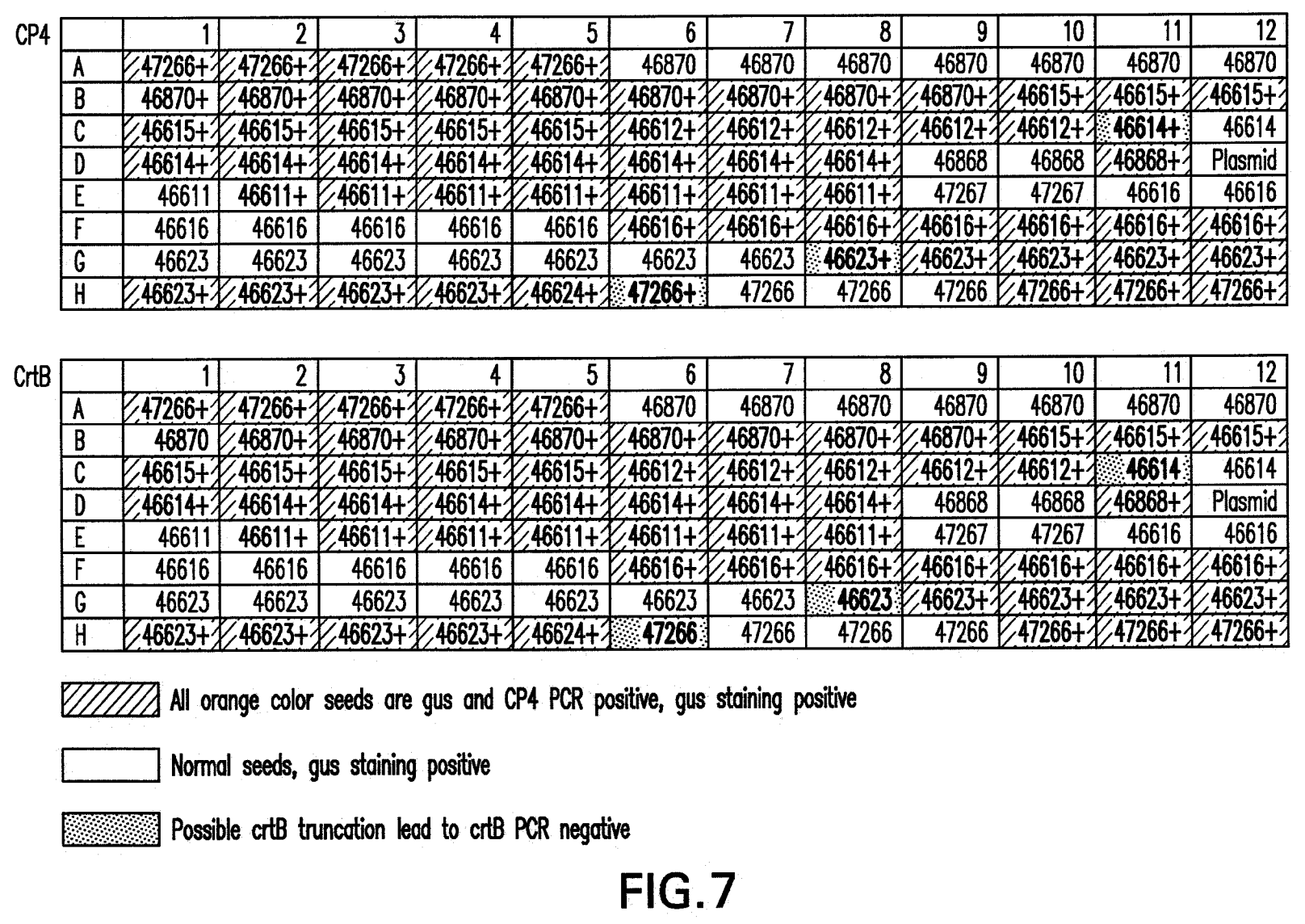

Additional events with plasmid pMON67465 were obtained by re-transformation of the plasmid into the same cultivar A3244 and 13 transgenic lines were obtained with transformation frequency of 0.22%. Seven out of 13 lines are gene of interest-positive and marker free after analyzing normal appearance seeds via PCR for presence or absence of a gus or CP4 marker gene (FIG. 6). The orange seeds from R0 plants were also analyzed by PCR for the presence of the crtB gene and CP4 marker gene. All orange seeds but three were found to be positive for both crtB and CP4 (FIG. 7), whereas none of normal appearance seeds (FIG. 7, white cells) contained CP4 or crtB genes, which indicated the crtB phenotype is tightly linked to the CP4 selectable marker gene.

Thus, use of a 2 T-DNA construct with an identification sequence including a screenable gene linked to a selectable marker gene allows for more efficient screening and selection of transgenic events containing a gene of interest while lacking sequences encoding a selectable marker. An exemplary comparison between a linkage-Southern based approach ("Standard 2T") and a label-based (i.e., identification sequence based) screen for identifying progeny seed in which a gene of interest and a selectable marker have independently segregated is found in FIG. 8. Use of the identification sequence approach allows for screening more transgenic events and more progeny of each event in order to identify progeny useful for further analysis.

Example 3

CrtB/GUS/CP4 Expression in Soy Event A33908 and R1 Progeny Seed

Figure 2:
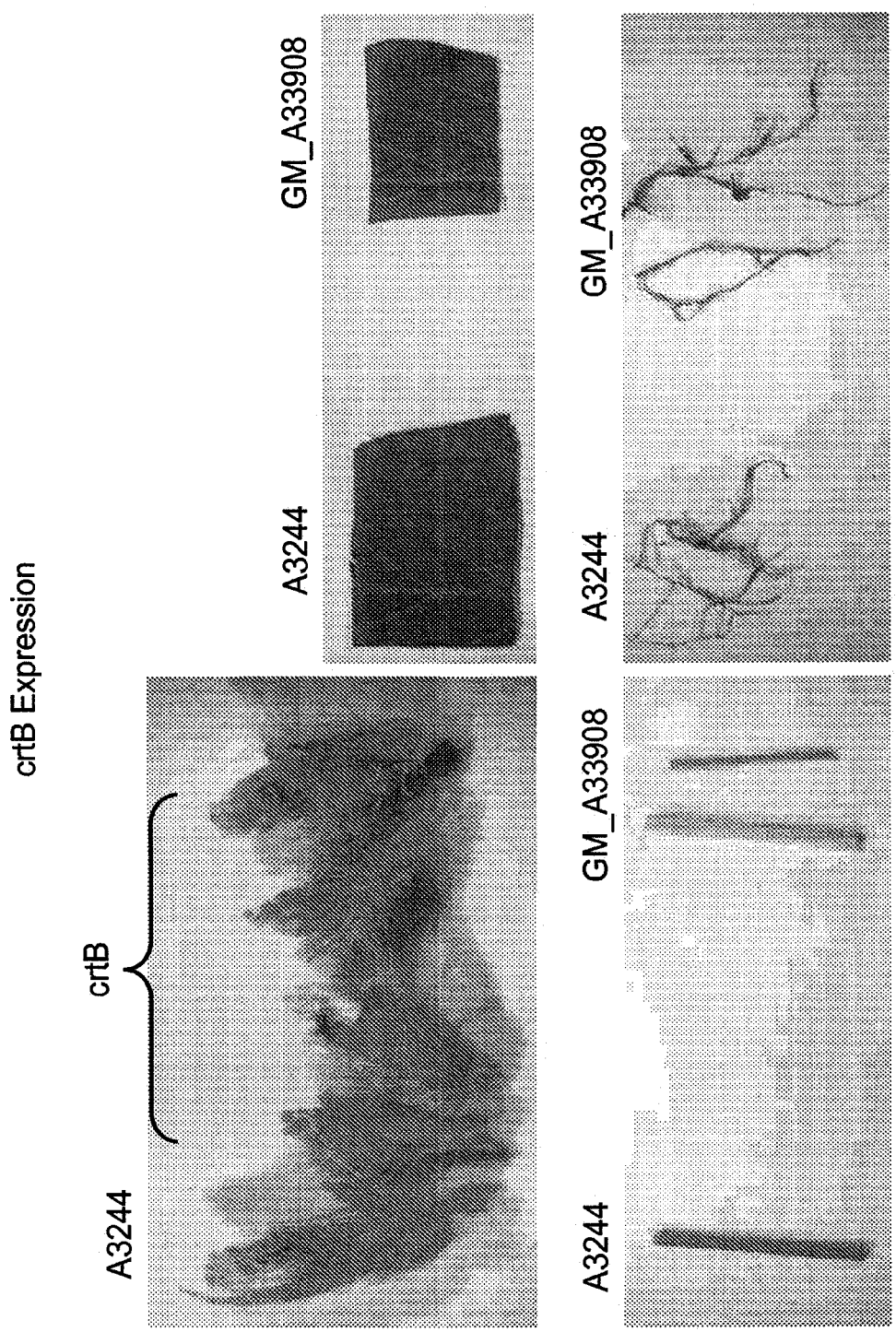
FIG. 2. CrtB expression in soybean tissues transformed with pMON67465.

Visual inspection of tissues from event A33908 (FIG. 2) indicated that stems and young unfolded leaves displayed an orange cast. Leaf and root tissue was otherwise phenotypically normal in CrtB-expressing plants. Seed coats from seed of the R0 plant (i.e. the R1 generation) displayed slight CrtB expression, while the cotyledons of A33908-derived seed displayed a distinct orange color and some with a wrinkled phenotype (FIG. 3).

Figure 4:
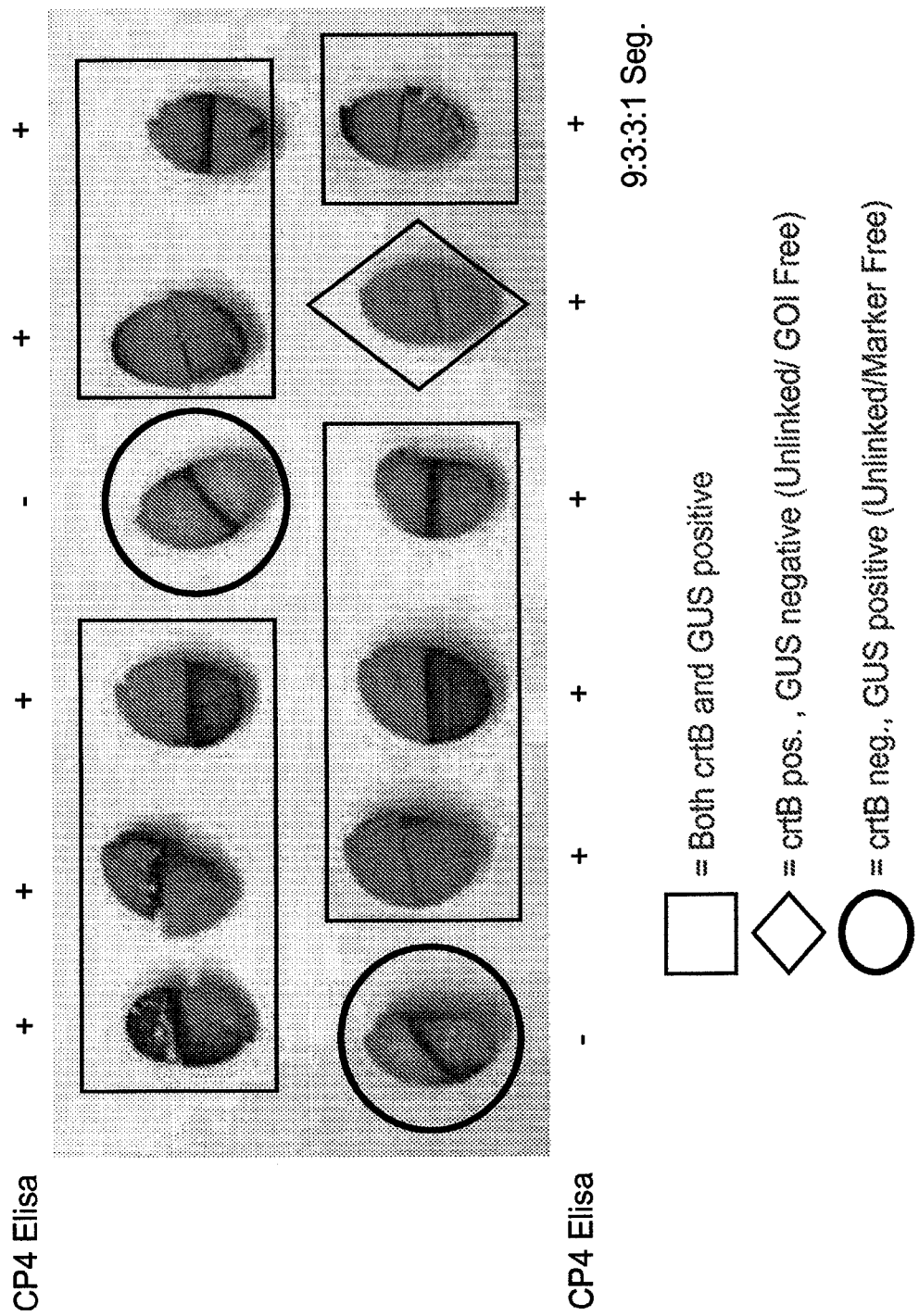
FIG. 4. Expression of crtB, gus, and CP4/EPSPS in immature R1 seed.

Twelve immature R1 seeds from event A33908 were dissected from the seed coat and subjected to CP4-EPSPS ELISA, and CrtB and GUS-visual analyses (FIG. 4). Segregation of the CrtB, GUS, and CP4-EPSPS phenotypes was evident. 9/12 seed were positive in all three assays. 1/12 seed was CrtB and CP4-EPSPS positive, but GUS negative, showing segregation of the two T-DNAs of pMON67465, with loss of the gus gene. 2/12 seed were CP4-EPSPS ELISA negative. Both of these seed were CrtB negative and GUS positive, thus demonstrating linkage between the identification sequence (crtB) and the selectable marker CP4-EPSPS gene, and segregation of these transgenic loci from the gus locus. The phenotypic ratio in segregating seed was consistent with Mendelian segregation of two dominant loci.

Example 4

R1 Seed Visual Analysis

Figure 5:
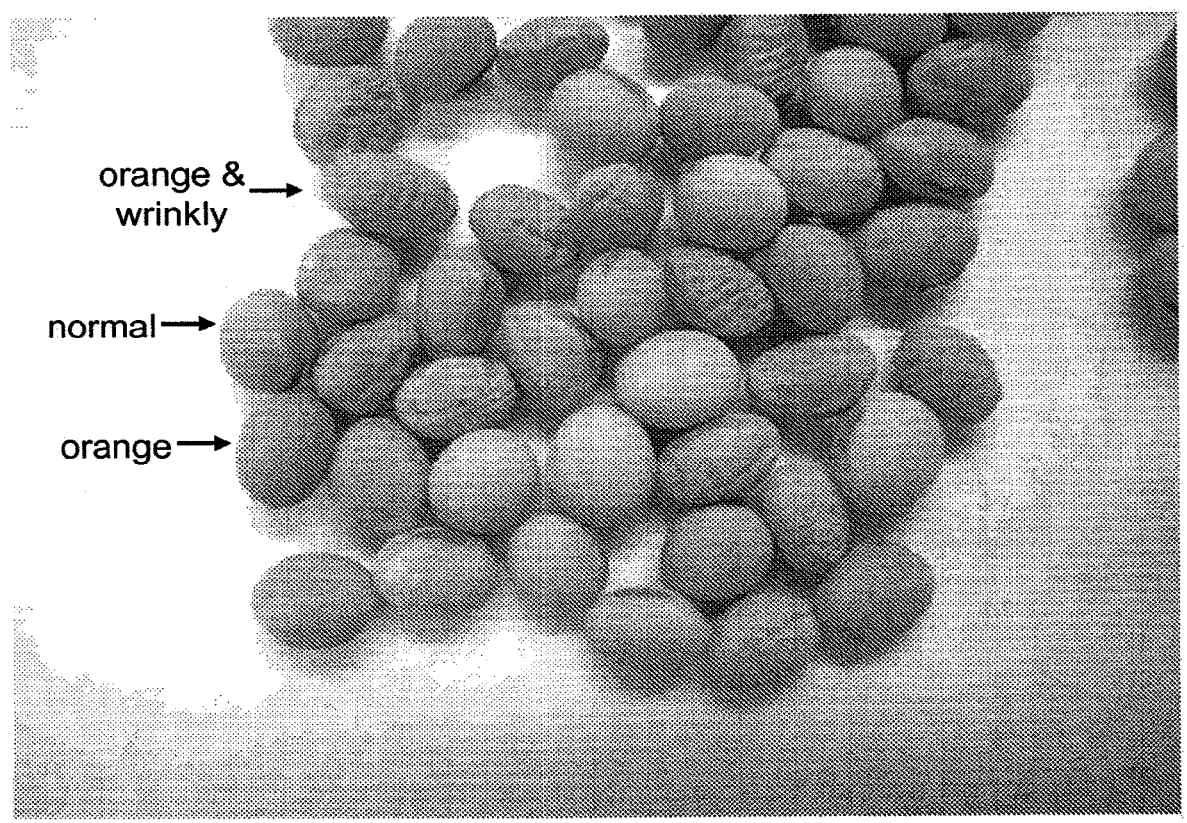
FIG. 5. Expression of crtB in mature R1 seed.

Mature seed from A33908 were visually analyzed for color, size, and shape (FIG. 5). A mixture of (i) marker-free normal (e.g. yellow and smooth); (ii) orange and smooth; and (iii) orange and shrunken seed was seen.

Example 5

PCR Analysis on GUS Positive Seed

INVADER PCR (e.g. Mein et al., 2000) was used to follow segregation of the CP4-EPSPS, crtB, and gus genes delivered by pMON67465 in seed of transgenic soybean plants. Event A33908 was determined to contain a single copy of the CP4-EPSPS marker gene and a single copy of the NPTII gene. Segregation of orange:normal seed followed an expected 3:1 ratio in event A33908 (Table 1).

TABLE 1

Phenotype and genotype of progeny of transgenic plants

| Pedigree | Invader CP4 | Invader NPT II | Orange/Normal seed count | Expect. 3:1 orange/normal seed count | Chi square |
|---|---|---|---|---|---|
| GM | 1 | 1 | 86/26 | 84/28 | 0.19 |
| GM | 2 | 1 | 98/56 | 115.5/38.5 | 10.61 |
| GM | 1 | 1 | 130/72 | 151.5/50.5 | 12.20 |
| GM | 1 | 2 | 134/56 | 142.5/47.5 | 2.03 |
| GM | 2 | 0 | 62/30 | 69/23 | 2.84 |
| GM | 1 | 2 | 77/25 | 76.5/25.5 | |
| GM A339 | 2 | 2 | 79/40 | 89.25/29.75 | 4.71 |
| GM A339 | 2 | 4 | 57/18 | 56.25/18.75 | 0.04 |

Example 6

Use of ATP PFK as an Identification Sequence

For starch-rich cereal grains including corn, manipulation of sugar/starch metabolism resulting in a phenotype of shrunken or abolished seed development may be utilized. Seed-specific expression of sacB (Caimi et al. 1996), or seed-specific expression of yeast ATP dependent phosphofructokinase (ATP PFK; e.g. GenBank Accession NC_003423, bases 2297466 . . . 2300294) in corn ears results in abolished kernel development (FIG. 12). The construct pMON99575 containing the CP4 selectable marker and ATP-PFK may be directly used for co-transformation with a one T-DNA construct containing a gene of interest by mixing cells of two Agrobacterium strains each including one of these constructs and transforming a plant cell with the mixed bacterial culture. Alternatively, the seed-specific expressing ATP PFK cassette may be subcloned into a 2T-DNA construct as an identification sequence, for efficient identification of marker free seeds. Kernels containing this gene are extremely shrunken and do not germinate. Only the identification sequence-free and marker gene free kernels show normal appearance.

Example 7

Use of Genes Involved in Porphyrin Synthesis as Identification Sequences

S-adenosyl-L-methionine-dependent uroporphyrinogen III (uro'gen) methyl transferases (SUMT) produce bright red fluorescent porphyrinoid compounds when overexpressed in *E. coli*, yeast, and CHO cells. This property has enabled visual selection of transformed *E. coli* colonies (Rossner & Scott 1995) and automated sorting of transformed yeast and CHO cells (Wildt & Deuschle 1999). This fluorescence is the result of intracellular accumulation of di- and tri-methylated uro'gen (dihydrosirohydrochlorin and trimethylpyrorocorphin), both of which are compounds found in porphyrin synthesis pathways (i.e., chlorophyll and cobalamin).

Cells transformed with cobA encoding SUMT from *Propionibacterium freudenreichii* (GenBank accession U13043; incorporated herein by reference) yield a fluorescent signal with absorbance peaks at 384 nm and 500 nm along with an emission band at 605 nm. The fluorescent porphyrinoids generated by the cobA uro'gen methyl transferase have a good spectral signature for marking plant material. Excitation at either 384 or 500 nm avoids strong chlorophyll absorbance and the resulting red emission is readily detected as it has a substantial Stokes shift (from the 500 nm absorbance origin), but does not overlap with chlorophyll autofluorescence in the far red (Haseloff, 1999).

The carboxy terminus of the maize SUMT (GenBank D83391), *Arabidopsis* Upm1 (GenBank L47479), and *E. coli* CysG (GenBank X14202) proteins are significantly similar to proteins encoded by genes of *P. freudenreichii* (cobA), *Pseudomonas* denitrificans (cobA; GenBank M59236), and of *Synechocystis* sp. (formerly *Anacystis nidulans*; GenBank X70966), each incorporated herein by reference (Sakakibara et al. 1996), and may be used similarly.

A construct including a promoter with kernel expression and a gene encoding CobA, or a similar protein with SUMT activity, allows the use of such a gene as an identification sequence by screening for (lack of) visible red fluorescence in corn seed, for instance. Plant siroheme synthases have been reported to be localized in the chloroplast (Leustek et al., 1997). Thus use of a porphyrin biosynthesis gene as an identification sequence may include use of a chloroplast transit peptide to direct the gene product to the chloroplast. The construct can be directly used as an identification sequence, and a T-DNA comprising such an identification sequence and a selectable marker may, for instance, be co-transformed with a second construct comprising a T-DNA containing a gene of interest by mixing two Agrobacterium strains each containing one of these constructs, and transforming a plant cell with the mixed bacterial culture. An SUMT expression cassette can also be readily subcloned into other 2 T-DNA vectors, or into a vector designed for use in microprojectile-mediated transformation, and used as an identification sequence by a person of skill in the art.

Example 8

Use of Gene Silencing to Produce a Detectable Seed Phenotype

Figure 9:
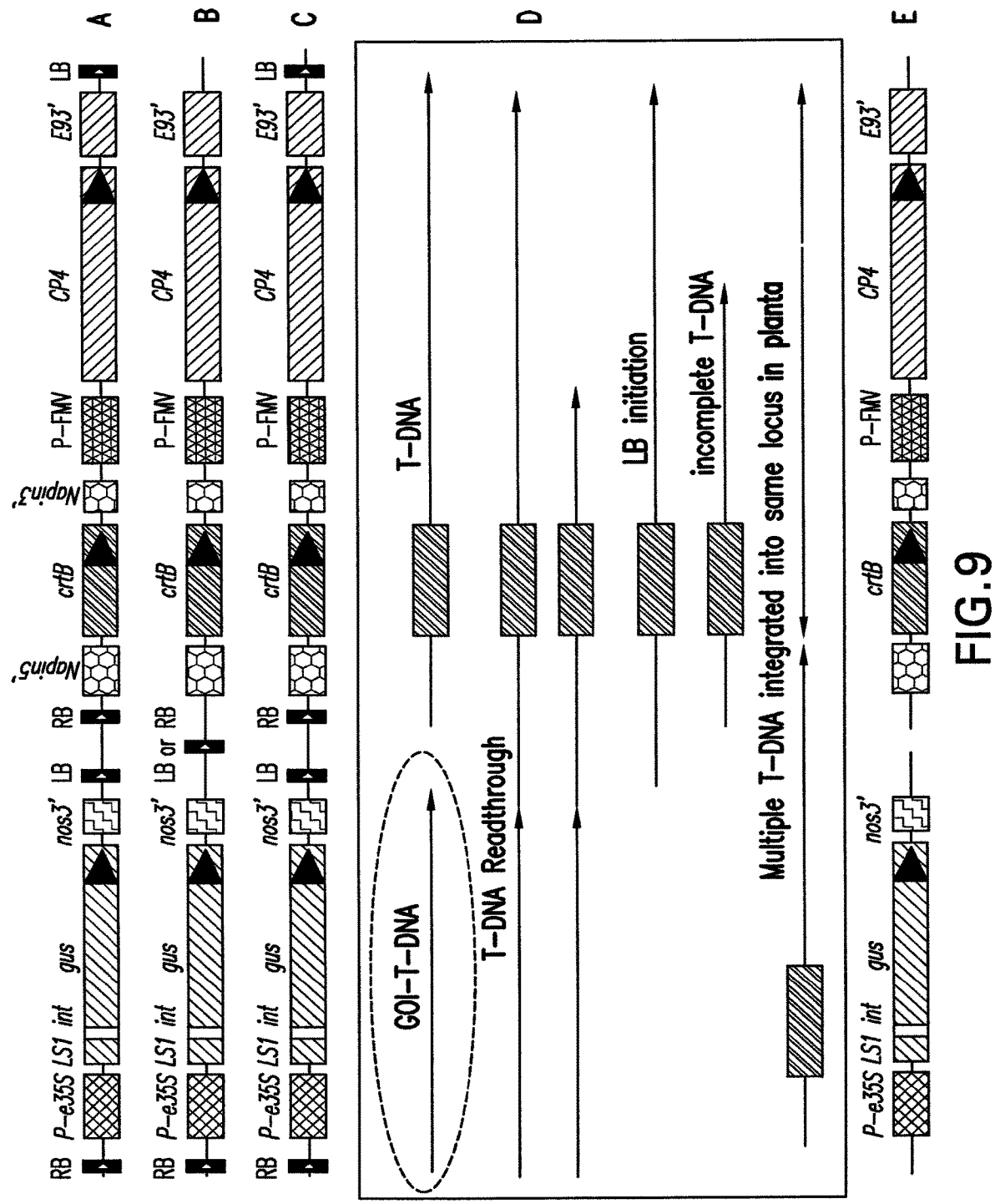
FIG. 9. Schematic summary of DNA sequences transferred by use of construct comprising a screenable gene linked to CP4 selectable marker genes for marker-free seeds. A) GOI located in one T-DNA flanked with a RB and LB and physically linked to a second T-DNA containing a screenable gene linked to a CP4 selectable marker gene in one construct used for *Agrobacterium*-mediated transformation; B) One vector containing two borders, the GOI is placed after a RB while the screenable and selectable marker genes are placed after the second RB or after a LB together with backbone; C) The GOI and screenable genes—DNAs are separated in two vectors and transformed in either one *Agrobacterium* cell or separate *Agrobacterium* cells; D) Possible linkage of two DNA segments from the GOI and screenable and selectable marker genes. Only the GOI alone will show normal seed appearance, while cells containing the screenable gene show a visible phenotype; E) Two separate DNA segments contain either the GOI or screenable and selectable marker genes used for non-bacterial mediated transformation.
Figure 10:
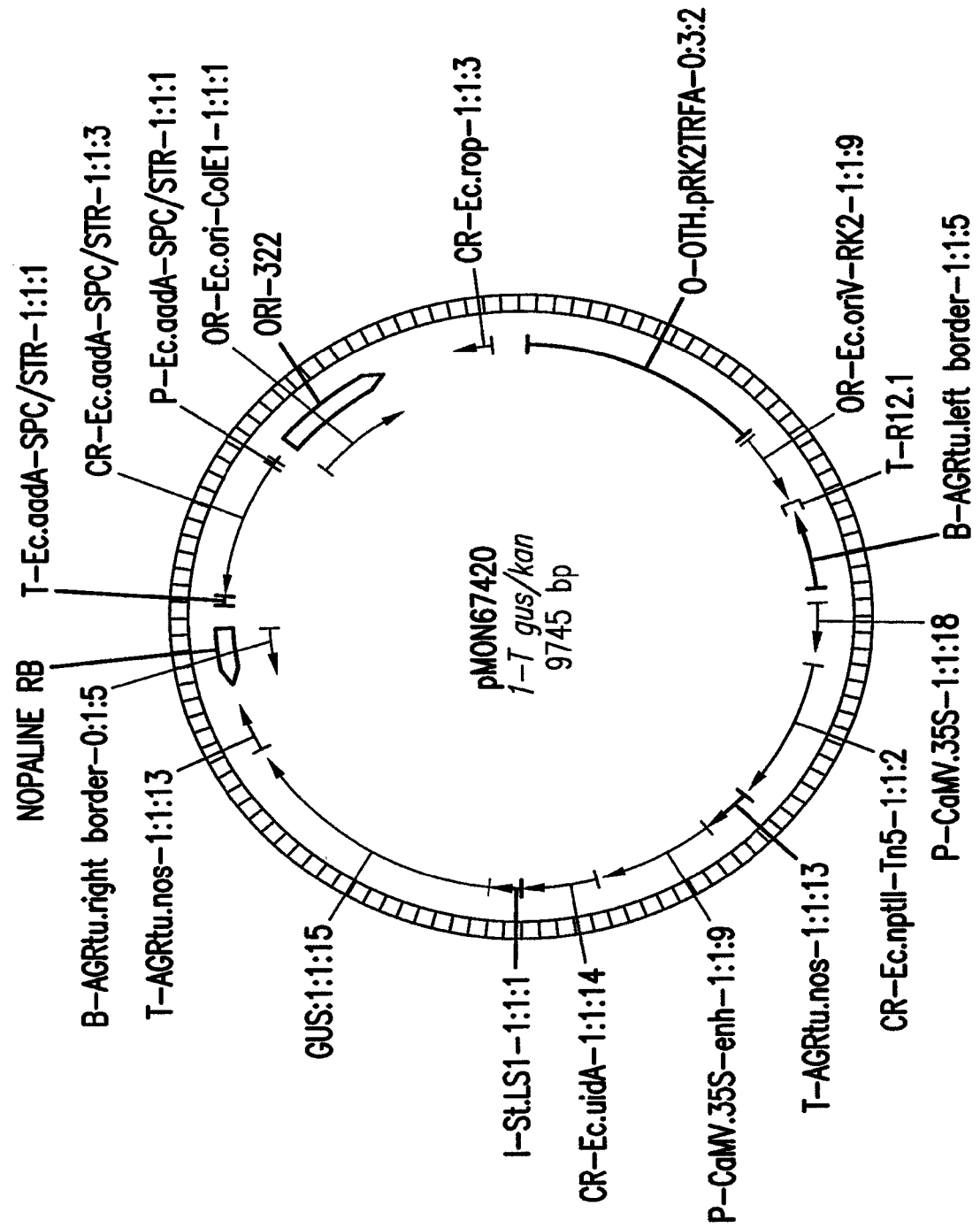
FIG. 10. pMON67420 represents a GOI construct for co-transformation.
Figure 11:
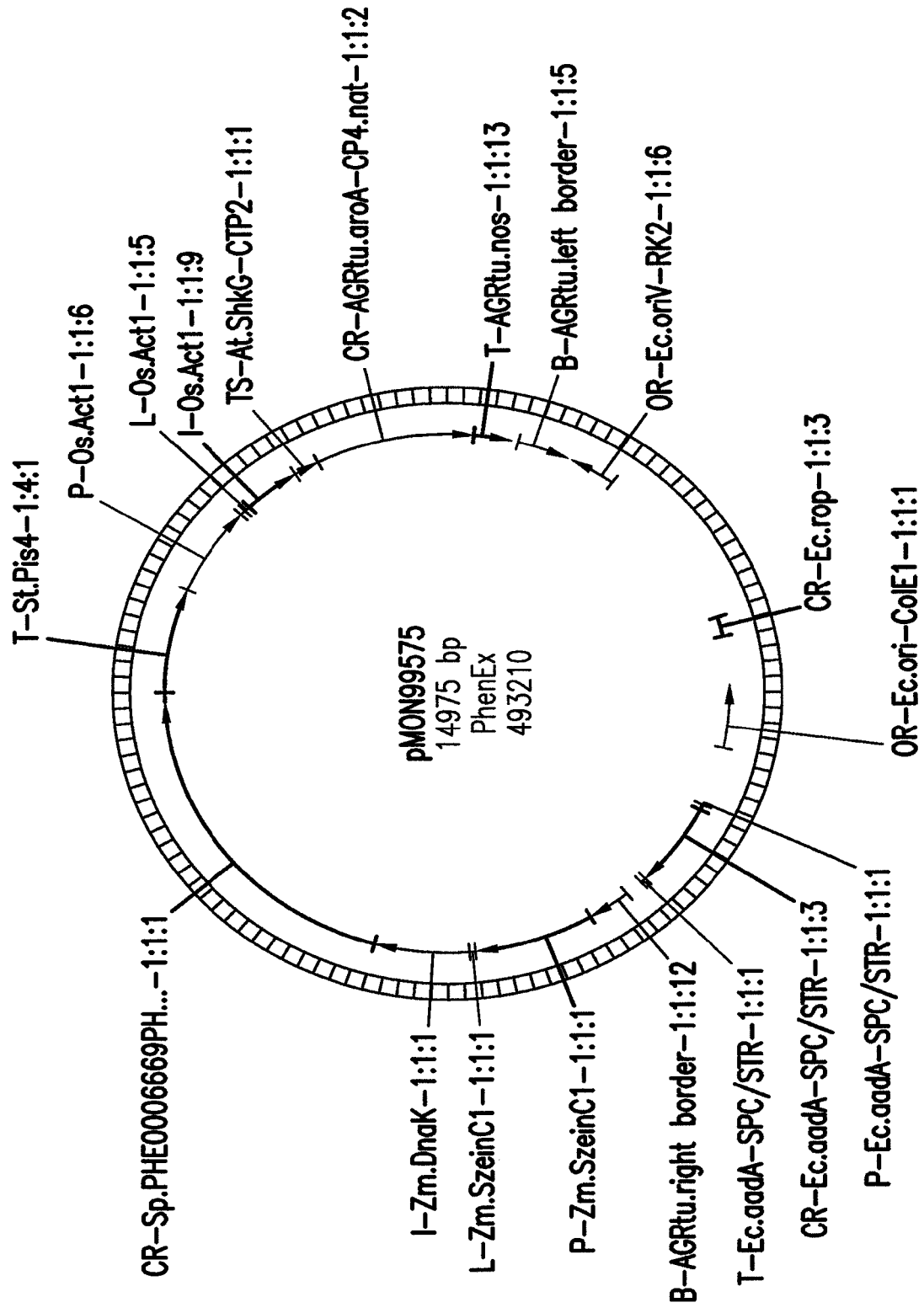
FIG. 11. Plasmid pMON99575 containing *Schizosaccharomyces pombe* ATP dependent phosphofructokinase driven by the seed-specific zein promoter.
Figure 13:
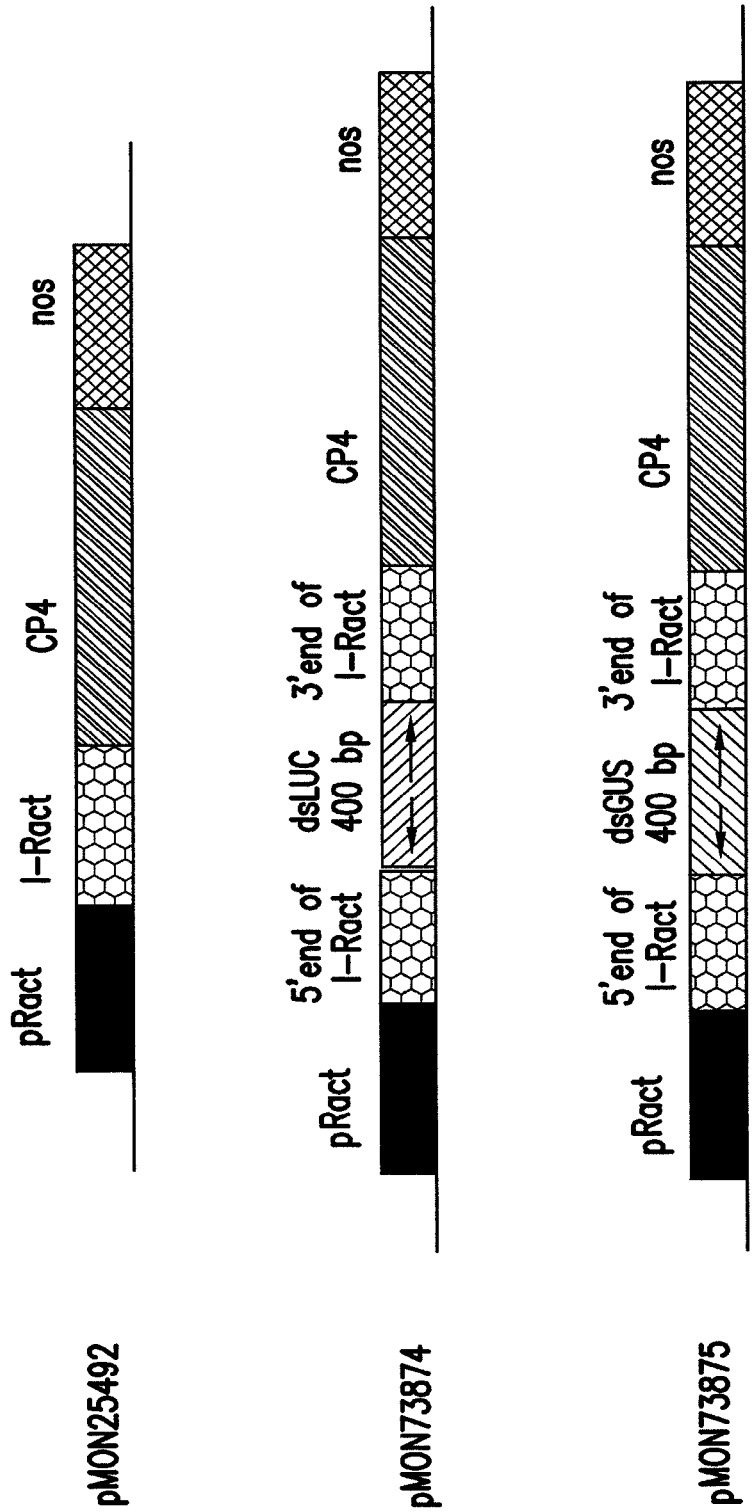
FIG. 13. Schematic diagram of dsRNA-encoding constructs used to demonstrate that inverted repeats placed within an intron of a marker gene result in a visible phenotype.

An inverted repeat positioned within an intron of the marker gene cassette can lead to efficient gene silencing in plant cells. This is disclosed in detail in U.S. Application Publication No. 2006/0200878 (e.g., FIGS. 7, 8, 9, incorporated herein by reference). To test if a dsRNA encoded by inverted repeats placed within an intron was capable of eliciting gene silencing, inverted repeats of a ~400 bp segment of the luciferase gene (SEQ ID NO:1) were placed into the intron of the rice Actin1 promoter in a EPSPS-CP4 gene cassette (pMON73874) and the ability of the construct to suppress the luciferase gene in a transient transformation of corn leaf protoplasts was tested. As a control, a similar plasmid was tested, except that the control plasmid had inverted repeats of a segment of the GUS gene instead of the luciferase gene (pMON73875). Finally, as an additional control, pMON25492, which was identical except that it has no inverted repeats, was also employed (FIG. 13).

Figure 14:
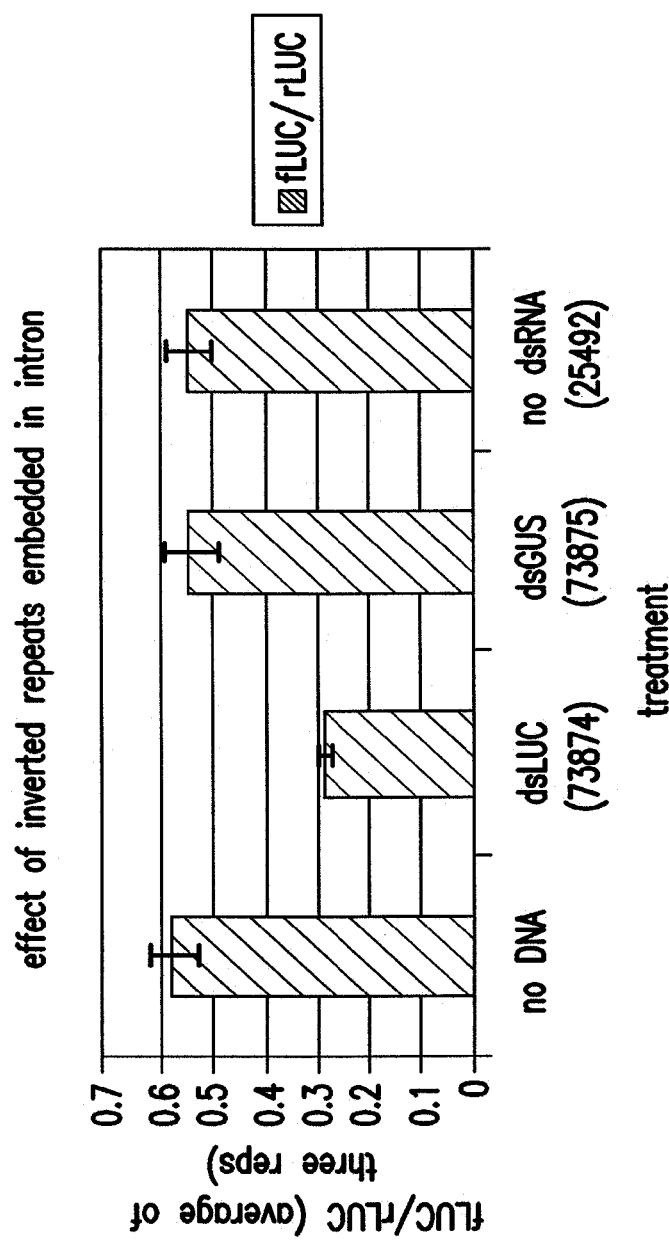
FIG. 14. Inverted repeats embedded in an intron give rise to a visible phenotype.

When these three plasmids were tested in a corn leaf protoplast transient gene silencing system testing for the suppression of firefly luciferase and normalizing to the expression of a RENILLA luciferase (Promega Corp., Madison, Wis.) internal control, it was observed that plasmid with dsRNA encoding inverted repeats within the intron (pMON73874) was able to suppress luciferase relative to the controls pMON73875 and pMON25492 (FIG. 14). The experiment was repeated a second time with similar results.

To test if a corn kernel phenotype may be generated via a gene silencing approach, constructs designed to suppress the Waxy gene were made. pMON81990 contains inverted repeats of part of the Waxy gene. Transgenic corn plants containing pMON81990 displayed silencing of the Waxy gene in at least 65% of the independent R0 plants, as determined by staining pollen and kernels with iodine for starch production. In comparison, plants containing pMON81993, which expresses a sense fragment of Waxy, do not display efficient silencing of the Waxy gene.

Figure 15:
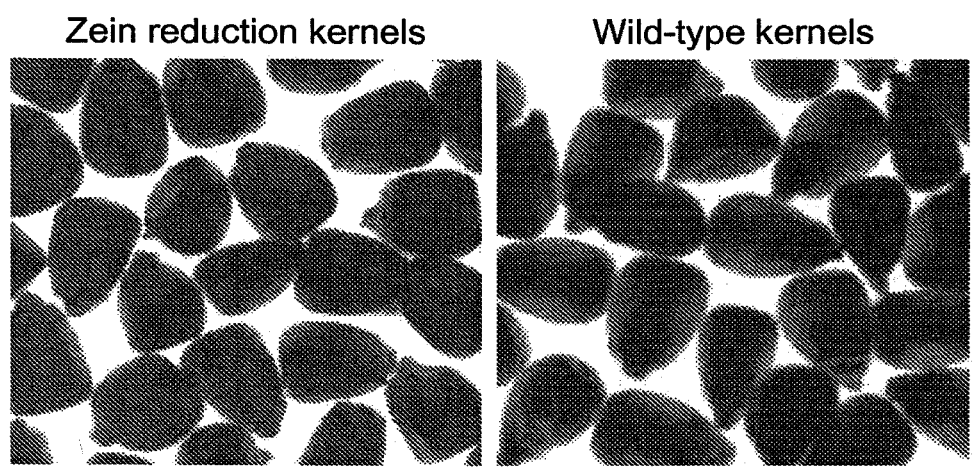
FIG. 15. Silencing of α-zeins in corn kernels leads to a visible phenotype.

Silencing of genes that encode zeins (seed storage proteins), leading to a visible phenotype was also demonstrated. pMON73567 contains inverted repeats of sequences of genes that encode α-zeins in corn kernels. Transcription of the inverted repeats results in silencing of these genes, reducing the levels of the 19 kD and 22 kD α-zeins in 26 out of 29 R0 plants tested. FIG. 15 demonstrates that kernels resulting from cells transformed with this dsRNA-encoding sequence have an obvious visual phenotype, wherein kernels with reduced zeins are less translucent than wild-type kernels.

Thus, a dsRNA-encoding sequence embedded in the intron of a marker gene may be used as an identification sequence according to the present invention. Constructs containing, for instance, a glyphosate resistance gene such as CP4 EPSPS as a selectable marker and such a dsRNA-encoding sequence in an intron of the selectable marker gene may be directly used for co-transformation with a one T-DNA construct containing a gene of interest by mixing cells of two Agrobacterium strains each comprising one of these constructs and transforming a plant cell with the mixed bacterial culture. Alternatively, the dsRNA-encoding cassette may be subcloned into a 2T-DNA construct as an identification sequence, for efficient identification of marker free seeds. One of skill in the art could also design analogous constructs for use in microprojectile bombardment-mediated plant cell transformation.

Example 9

Use of KAS4 as an Identification Sequence

Figure 16:
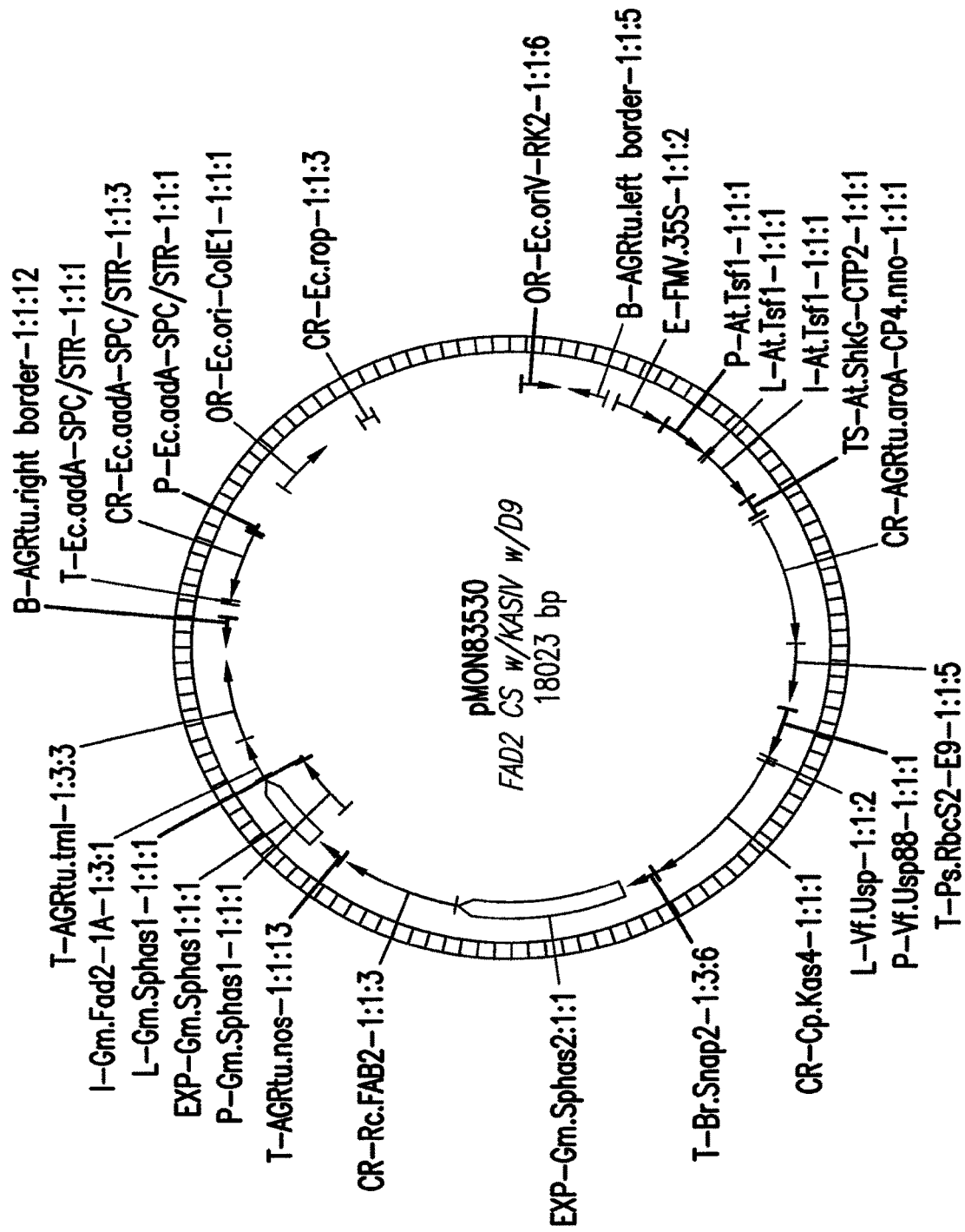
FIG. 16. Schematic diagram of pMON83530 containing KAS4.
Figure 17:
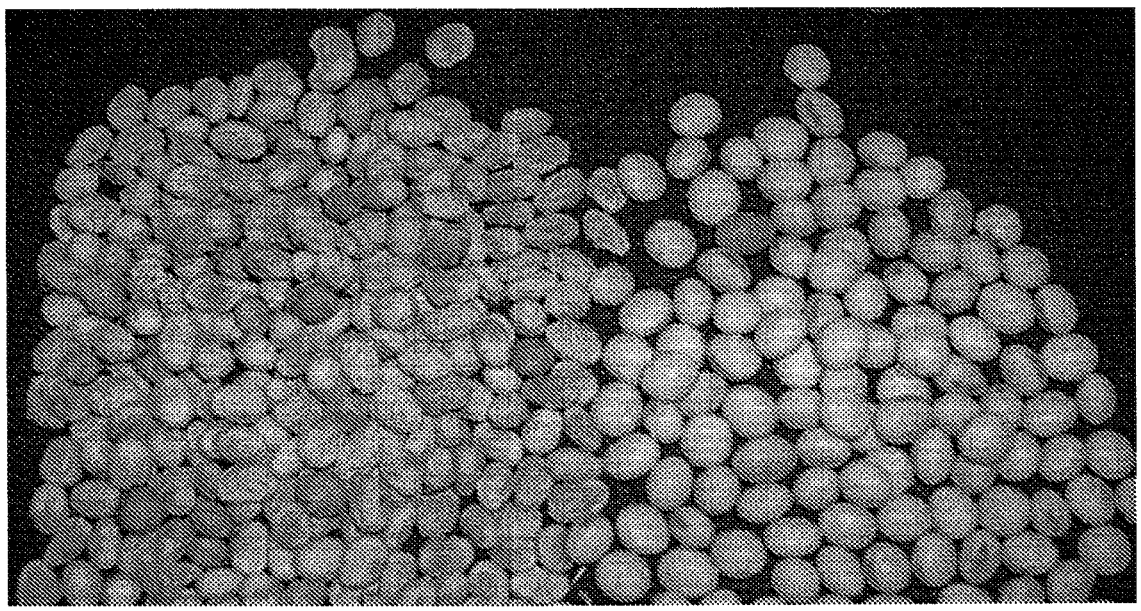
FIG. 17. Progeny of soybean seeds transformed with pMON83530. Seeds on the left are shrunken due to expression of KAS4 and indicate the presence of selectable marker, while seeds on the right are normal and marker-free.

Binary vector pMON83530 (FIG. 16) contains a KAS4 (a-keto-acetyl-ACT synthase; GenBank accession AF060518) driven by a soybean USP88 promoter (e.g. U.S. Pat. No. 7,078,588) with a CP4 plant expressible cassette as a selectable marker on the same T-DNA. The seed-specific expression of the KAS4 gene results in shrunken seeds which are easily distinguishable from the normal seeds which do not contain the gene (FIG. 17). The construct can be directly used as an identification sequence, and a T-DNA comprising such an identification sequence and a selectable marker may be co-transformed with a second construct comprising a T-DNA containing a gene of interest by mixing two Agrobacterium strains each containing one of these constructs and transforming a plant cell with the mixed bacterial culture.

Figure 18:
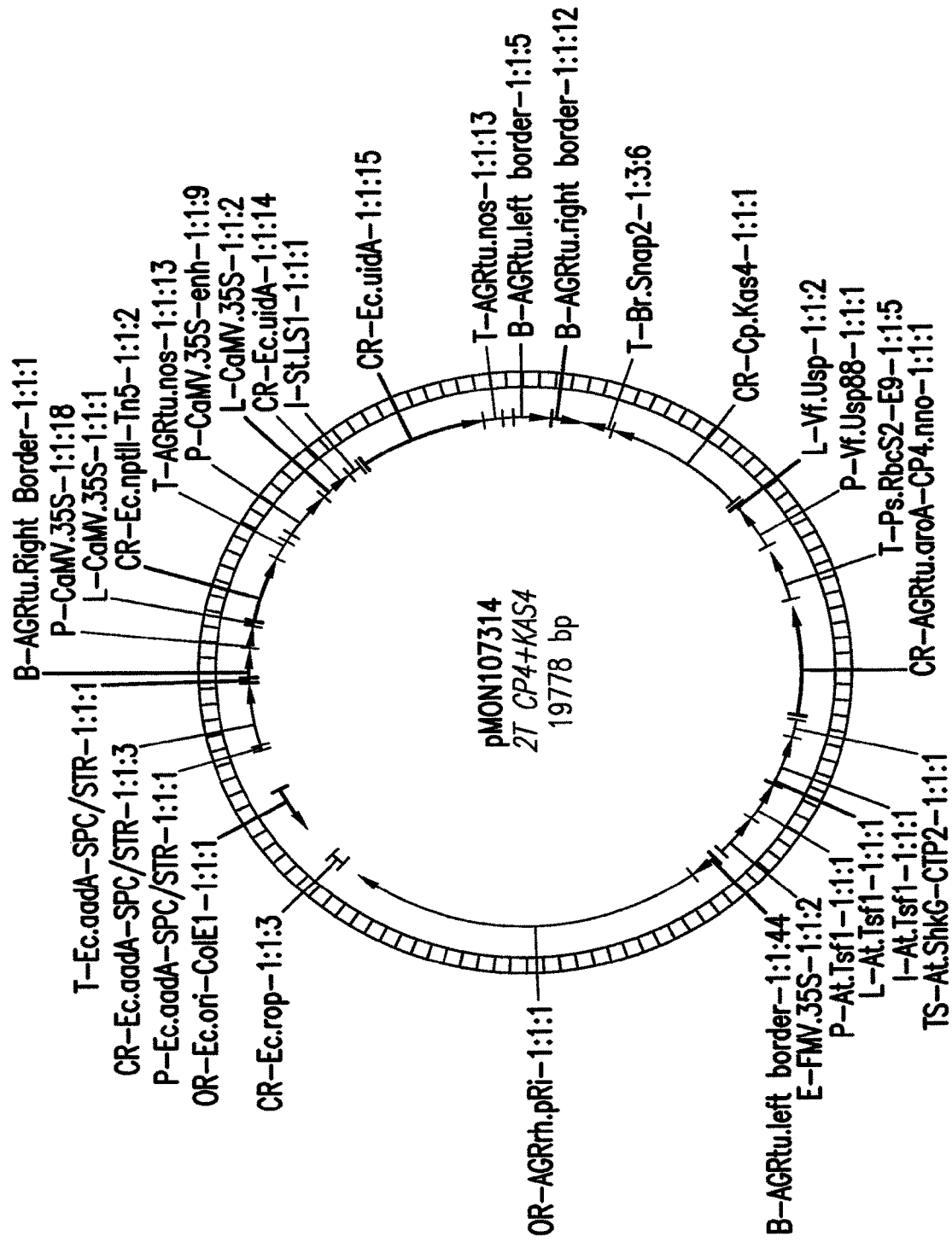
FIG. 18. Schematic diagram of pMON107314 containing KAS4 useful as an identification sequence in a 2T DNA construct.

The KAS4 expression cassette is also present in a 2 T-DNA plasmid as shown in pMON107314 (FIG. 18) wherein one T-DNA comprises a splA gene (Sucrose phosphorylase from Agrobacterium tumefaciens; GenBank Accession AE009432) as an identification sequence and a marker gene and the other T-DNA may comprise a gene of interest as constructed by routine cloning methods known to those skilled in the art. The 2 T-DNA plasmid can then be used, for instance, for soybean transformation. The identification gene is used for selecting seeds without marker gene based on phenotype provided by the identification gene.

Example 10

Use of an splA Gene as an Identification Sequence

Figure 19:
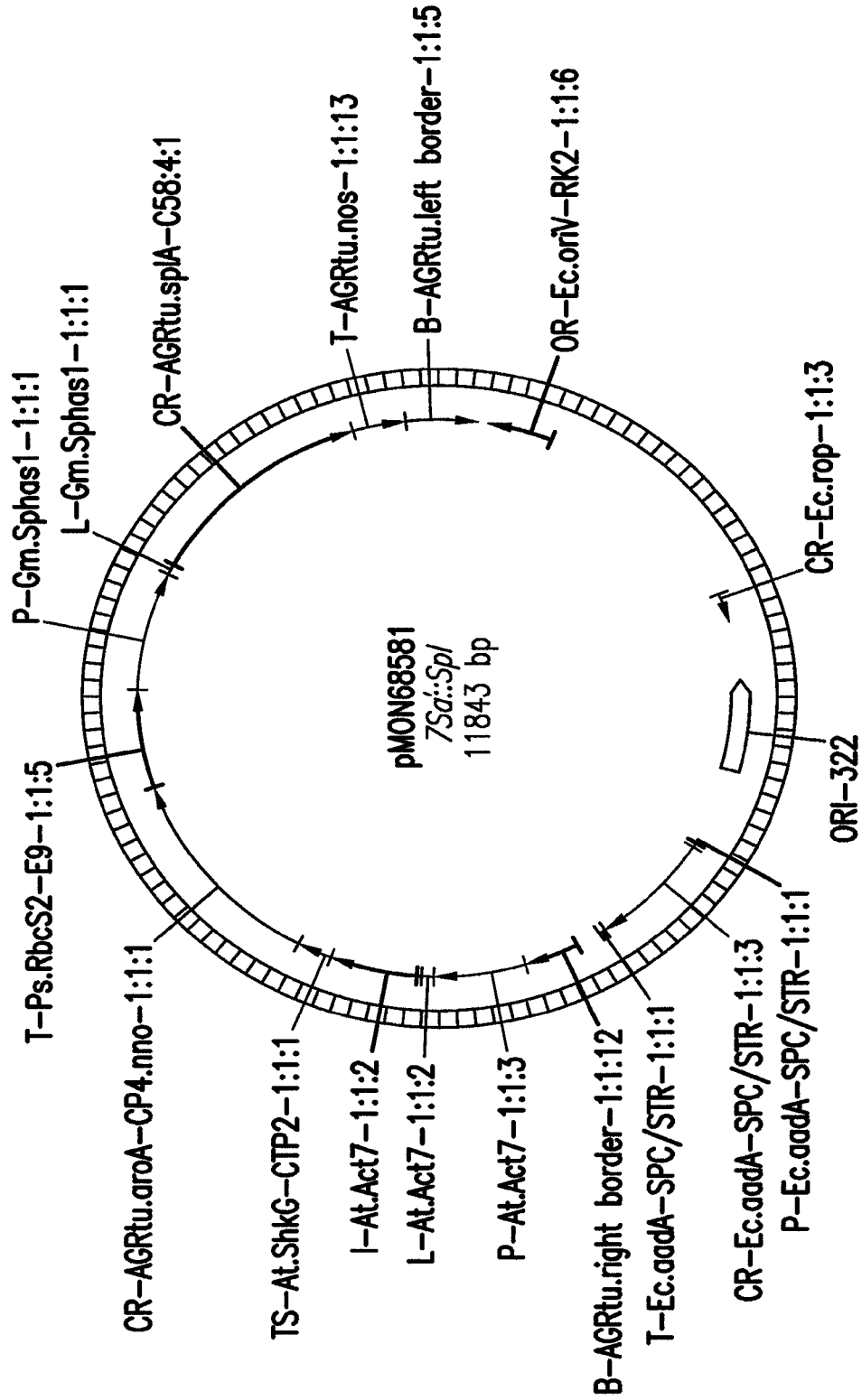
FIG. 19. Schematic diagram of pMON68581 containing a splA gene useful as an identification gene.
Figure 20:
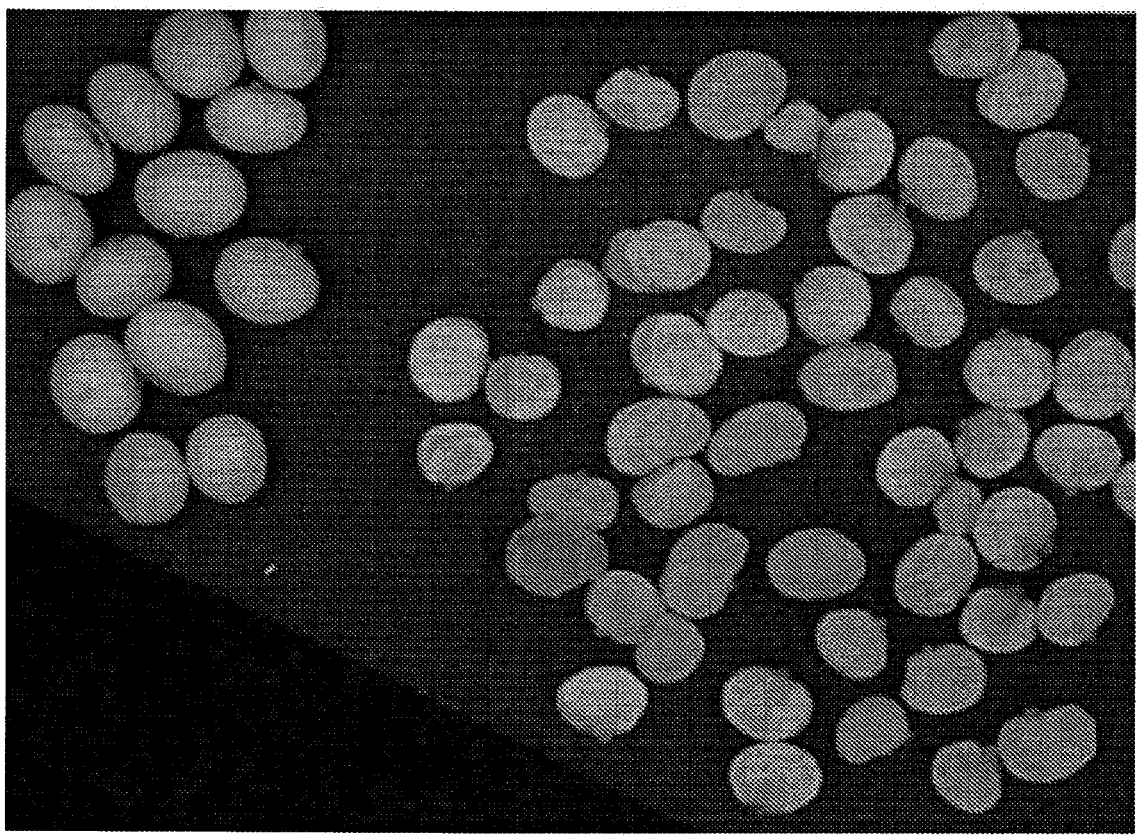
FIG. 20. Progeny soybean seeds transformed with pMON68581. Seeds on the right are shrunken due to the expression of splA and indicate the presence of the screenable or selectable marker, while seeds on the left are normal and marker-free.

Binary vector pMON68581 (FIG. 19) contains the splA (Sucrose phosphorylase from Agrobacterium tumefaciens; GenBank Accession AE009432) driven by a soybean 7S alpha promoter (e.g. GenBank M13759; Doyle et al., 1986) with a CP4 plant expressible cassette as a selectable marker on the same T-DNA. The seed-specific expression of the splA gene results in shrunken seeds which are easily distinguishable from the normal seeds which do not contain the gene (FIG. 20). The construct can be directly used as an identification sequence, and a T-DNA comprising such an identification sequence and a selectable marker may be co-transformed with a second construct comprising a T-DNA containing a gene of interest by mixing two Agrobacterium strains each containing one of these constructs and transforming a plant cell with the mixed bacterial culture. The splA expression cassette can also be readily sub-cloned into 2 T-DNA vectors wherein one T-DNA comprises splA gene as an identification sequence and a marker gene and the other T-DNA comprises a gene of interest by routine cloning methods known to those skilled in the art. The 2 T-DNA plasmid can then be used, for instance, for soybean transformation. The identification sequence is used for selecting seeds without a selectable or screenable marker gene based on the phenotype phenotype provided by the identification sequence.

Example 11

Use of Several Identification Sequences in Producing Marker-Free Corn Seed

Multiple 2 T-DNA plant expression vectors were constructed. In each construct, the first T-DNA segment comprised a plant expressible uidA transgene as an example of a nucleic acid of interest and the second T-DNA segment comprised of a plant expressible CP4 EPSPS transgene as a selectable marker and an identification sequence as shown in the table below. Sequences of crtB designed for expression in monocots were prepared by methods known in the art (e.g. by codon-optimization as found in SEQ ID NO:2; SEQ ID NO:3). pMON68412 comprises SEQ ID NO:3. The first T-DNA is flanked by right and left borders while the second T-DNA is a located in the vector backbone, a 2 T-DNA format commonly known as tandem format (Huang et al., 2005). Corn tissues were transformed separately with each of the constructs by methods known in the art. The expected phenotype with each identification gene is indicated in Table 2 below. Alternative promoters for expression of the identification sequences in endosperm include glutelin1 promoter from rice, the waxy promoter from corn, and the brittle2 promoter from corn.

TABLE 2

Exemplary phenotypes expected with given identification sequences.

| Identification Sequence Cassette | | | | Phenotype of seeds carrying the identification gene and the selectable marker gene |
|---|---|---|---|---|
| Promoter | Identification sequence | Terminator | Construct | |
| Maize 27 kD zein | crtB | Rice Glutelin 1 | pMON68412 | carotenoid pigment in endosperm; defective kernel development |
| Maize 27 kD zein | 19 & 22 kD zein inverted repeats (US 20060200878) | Rice Glutelin 1 | pMON68413 | opaque endosperm |
| Maize 27 kD zein | Phosphofructokinase (pfk) | Rice Glutelin 1 | pMON68414 | shrunken endosperm |
| Maize 27 kD zein | B peru | Rice Glutelin 1 | pMON68415 | anthocyanin pigment in endosperm |
| None | None | None | pMON97371 | none |

All of the compositions and methods disclosed and claimed herein can be made and executed without undue experimentation in light of the present disclosure. While the compositions and methods of this invention have been described in terms of the foregoing embodiments and illustrative examples, it will be apparent to those of skill in the art that variations, changes, modifications, and alterations can be applied to the composition, methods, and in the steps or in the sequence of steps of the methods described herein, without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. Nos. 4,940,835; 4,940,838; 4,946,046; 4,971,908; 5,015,580; 5,145,783; 5,188,642; 5,302,523; 5,310,667; 5,362,865; 5,384,253; 5,429,939; 5,464,763; 5,464,765; 5,508,184; 5,538,880; 5,545,816; 5,550,318; 5,563,055; 5,591,616; 5,633,435; 5,693,512; 5,731,179; 5,824,877; 5,859,347; 5,981,840; 6,160,208; 6,307,123; 6,326,527; 6,384,301; 6,399,861; 6,403,865; 6,429,356; 6,433,252; 6,458,594; 6,583,338; 6,803,501; 6,825,398; 7,078,588; 7,119,187; 7,151,204.

U.S. Pub. 20030110532; U.S. Pub. 20030229918; U.S. Pub. 20040237142; U.S. Pub. 20060041956; U.S. Pub. 20060064772; U.S. Pub. 20060200878

PCT Appln. WO 00/018939
PCT Appln. WO 97/41228
An et al., *Plant Physiol.*, 88:547, 1988.
An et al., *The Plant Cell*, 1:115, 1989.
Anderson et al., *Gene* 97:199-205, 1991.
Ausubel et al., In: *Current Protocols in Molecular Biology*, John, Wiley & Sons, Inc, New York, 1992.
Baerson et al., *Plant Mol. Biol.*, 22(2):255-267, 1993.
Belanger and Kriz, *Genet.*, 129:863-872, 1991.
Bohlmann et al., *Plant J.* 7 (3): 491-501, 1995.
Breitler et al., *Transgenic Res.*, 13:271-287, 2004.
Broothaerts et al., *Nature* 433:629-633, 2005.
Bustos et al., *Plant Cell*, 1:839-853, 1989.
Caimi et al., *Pl. Physiol.* 110:355-363, 1996
Callis et al., *Plant Physiol.*, 88:965, 1988.
Carmi et al. *Planta*, 217:726-735, 2003.
Chen et al., *Dev. Genet.*, 10:112-122, 1989.
Chen et al., *Proc. Natl. Acad. Sci. USA*, 83:8560-8564, 1986.
Clark et al., In: *Plant Molecular Biology*, A Laboratory Manual, Springer, N.Y., 1997.
Clark et al., *Plant Mol. Biol.*, 16 (6): 1099-1101, 1991.
Coruzzi et al., *EMBO J.*, 3:1671-1679, 1984.
Dale et al., *Proc. Natl. Acad. Sci. USA*, 88:10558-10562, 1991.
Daley et al., *Plant Cell Reports*, 17:489-496, 1998.
De Neve et al., *Plant J.*, 11:15-29, 1997.
de Vetten et al., *Nat. Biotechnol.* 21:439-442, 2003.
DeBlock et al., *Theor. Appl. Genet.*, 82:257-263, 1991.
Dekeyser et al., *Plant Cell*, 2(7):591-602, 1990.
della-Cioppa et al., *Proc. Natl. Acad. Sci. USA*, 83:6873-6877, 1986.
Dellaporta et al., *Stadler Symposium*, 11:263-282, 1988.
Depicker et al., *Mol. Gen. Genet.*, 201:477-484, 1985.
Dinkova et al. *Plant J.* 41:722-31, 2005.
Doyle et al., *J. Biol. Chem.* 261:9228-9238, 1986.
Ebinuma et al., *Proc. Natl. Acad. Sci. USA*, 94:2117-2121, 1997.
Elliot et al., *Plant cell Rep.*, 18:707-714, 1999.
Eyal et al., *Plant Cell*, 7:373-84, 1995.
Fraley et al., *Proc. Natl. Acad. Sci. USA*, 80:4803-4807, 1983.
Framond et al., *Mol. Gen. Genet.* 202:125-131, 1986.
Fromm et al., *Plant. Cell*, 1(10):977-84, 1989.
Gallie et al., *The Plant Cell*, 1:301-311, 1989.
Gardiner et al., *Plant Physiol.*, 134: 1317-1326, 2004.
Gasser et al., *J. Biol. Chem.*, 263: 4280-4287, 1988.
Gelvin et al., In: *Plant Molecular Biology Manual*, Kluwer Academic Publishers, 1990.
Giroux et al., *Plant Physiol.*, 106:713-722, 1994.
Gordon-Kamm, et al., *Plant Cell* 2:603-618, 1990.

Gruber et al., In: *Vectors for Plant Transformation*, Methods in Plant Molecular Biology and Biotechnology, Glick and Thompson (Eds.), CRC Press, Inc., Boca Raton, 89-119, 1993.
Hajirezaie et al., *Potato Res.* 42:353-372, 1999.
Halpin, *Pl. Biotechnol. J.* 3:141-155, 2005.
Hanson et al., *Plant J.* 19:727-734, 1999.
Hare and Chua, *Nature Biotechnol.* 20:575-580, 2002.
Haseloff, *Methods in Cell Biology*, V58:139-151, 1999.
Heim and Tsien, *Curr. Biol.*, 6(2):178-182, 1996.
Himi et al. *Genome* 48:747-754, 2005.
Hong et al., *Plant Mol. Biol.*, 34(3):549-555, 1997.
Horsch et al., *Science*, 227:1229, 1985.
Huang et al., *Transgenic Research*, 13: 451, 2004.
Ikatu et al., *Bio/Technol.*, 8:241-242, 1990.
Jefferson et al., *EMBO J.*, 6:3901-3907, 1987b.
Jefferson et al., *Plant Mol. Biol, Rep.*, 5:387-405, 1987a.
Jofuku et al. *Proc. Nat. Acad. Sci. USA*, 102:3117-3122, 2005
Kaeppler et al., *Plant Cell Reports*, 9:415-418, 1990.
Katz et al., *J. Gen. Microbiol.*, 129:2703-2714, 1983.
Klee et al., *Mol. Gen. Genet.*, 210:437-442, 1987.
Kobayashi et al. *Planta*, 215:924:933, 2002
Kohno-Murase et al., *Plant Mol. Biol.*, 26:1115-1124, 1994.
Komari et al., *Plant J.*, 10:165-174, 1996.
Kononov et al., *Plant J.* 11:945-957, 1997.
Kridl et al., *Seed Sci. Res.*, 1:209:219, 1991
Kuhlemeier et al., *Plant Cell*, 1:471, 1989.
Leustek et al., *J. Biol. Chem.*, 272:2744-2752, 1997.
Lewin, In: *Genes V*, Oxford University Press, NY, 1994.
Ludwig et al., *Proc. Natl. Acad. Sci. U.S.A.*, 86:7092, 1989.
Marcotte et al., *Plant Cell*, 1:969, 1989.
Mazur, et al., *Nucleic Acids Res.*, 13:2373-2386, 1985.
McKnight et al., *Plant Mol Biol.*, 8:439-445, 1987.
Mein et al., *Genome Res*, 10:330-343, 2000.
Mendoza et al. *FEBS Letters*, 579:4666-4670, 2005.
Miki et al., In: *Methods in Plant Molecular Biology and Biotechnology*, Glick and Thompson (Eds.), CRC Press, Inc., Boca Raton, 1993.
Miki and McHugh, *J. Biotechnol.*, 107:193, 2004.
Misawa et al., *J. Bacteriol.*, 172:6704-6712, 1990.
Mizukami and Fisher, *Proc. Natl. Acad. Sci. USA*, 97:942-947, 2000.
Moloney et al., *Plant Cell Reports*, 8:238, 1989.
Morello et al. *Transgenic Res.* 9:453-462, 2000.
Odell et al., *Nature*, 313:810-812, 1985.
Okagaki, *Plant Mol. Biol.*, 19: 513-516, 1992.
Okita et al., *J Biol Chem.* 264:12573 1989.
Omirulleh et al., *Plant Mol. Biol.*, 21:415-28, 1993.
Ow et al., *Science*, 234:856-859, 1986.
Pang et al., *Plant Physiol.*, 112: 893-900, 1996.
Padgette, et al., *Crop Sci.* 35: 1451-1461, 1995.
Pedersen et al., *Cell*, 29:1015-1026, 1982.
Petit et al., *Mol. Gen. Genet.*, 202:388-393, 1986.
Poirier et al., *Theor. Appl. Genet.*, 100:487-493, 2000.
Potrykus et al., *Mol. Gen. Genet.*, 199:183-188, 1985.
Puchta, *Pl. Cell Tiss. Org. Cult.* 74:123-143, 2003.
Radchuk et al., *Plant Physiol.*, 140:263-278, 2006.
Rieger et al., In: *Glossary of Genetics: Classical and Molecular*, 5th Ed., Springer-Verlag, NY, 1991.
Riggs et al., *Plant Cell*, 1(6):609-621, 1989.
Roshal et al., *EMBO J.*, 6:1155, 1987.
Rossner and Scott, *BioTechniques*, V19(5):760-764, 1995.
Rotino et al. *Nat. Biotechnol.* 15:1398-141, 1997.
Russell and Fromm, *Transgenic Res.*, 6:157-68, 1997.
Sakakibara et al., *Plant J.*, V10(5):883-892, 1996.
Sambrook et al., In: *Molecular cloning: a laboratory manual*, 2nd Ed., Cold Spring Harbor Laboratory Press, Cold Spring Harbor, N.Y., 1989.
Sandmann and Misawa, *FEMS Microbiol Lett.*, 69(3):253-257, 1992.
Sato et al., *Crop Sci.* 44:646-652, 2004.
Schaffner and Sheen, *Plant Cell*, 3:997, 1991.
Schellmann et al., *EMBO J.* 21, 5036-5046, 2002.
Schernthaner et al., *EMBO J.*, 7:1249, 1988.
Schruff et al. *Development*, 133:251:261, 2006.
Scutt et al., *Biochimie* 84: 1119-1126, 2002.
Selinger et al. *Genetics*, 149:1125-1148, 1998.
Shewmaker et al., *Plant J.*, 20(4):401-412, 1999.
Shure et al., *Cell* 35:225-233, 1983.
Siebertz et al., *Plant Cell*, 1:961, 1989.
Simpson et al., *EMBO J.*, 4:2723, 1985.
Slocombe et al., *Plant Physiol.*, 104(4):167-176, 1994.
Stacey et al., *Plant Mol. Biol.*, 31:1205-1216, 1996
Sutcliffe et al., *Proc. Natl. Acad. Sci. USA*, 75:3737-3741, 1978.
Terada et al., *Mol. Gen. Genet.*, 220:389-392, 1990.
Thornburg et al., *Proc. Natl. Acad. Sci. USA* 84, 744-748, 1987.
Toro et al., *Proc. Natl. Acad. Sci. USA*, 85:8558-8562, 1989.
Walker et al, *Plant Biotechnol J.* 5:413-21, 2007.
Wildt and Deuschle, *Nature Biotechnology*, V17:1175-1178, 1999
Xing et al., *In Vitro Cell Devel. Biol. Plant* 36:456-463, 2000.
Yang et al. *Proc. Natl. Acad. Sci. USA*, 87:4144-4148, 1990.
Yoder et al., *Bio/Technology* 12:263-268, 1994.
Zheng et al., *Mol. Cell Biol.*, 13:5829-5842, 1993.
Zhou et al., *Acta Botanica Sinica* 45:1103-1108, 2003.
Zukowsky et al., *Proc. Natl. Acad. Sci. USA*, 80:1101-1105, 1983.

What is claimed is:

1. A DNA construct comprising
   (a) a first DNA segment comprising a gene of interest; and
   (b) a second DNA segment comprising a promoter functional in a seed operably linked to a DNA cassette that confers a detectable phenotype in seeds comprising the DNA cassette and a marker gene operably linked to a promoter functional in plants; further wherein the detectable phenotype comprises a change of: seed size, seed opacity, seed germinability, seed viability, seed shape, or seed texture.

2. The DNA construct of claim 1, wherein the marker gene is a selectable marker gene.

3. The construct of claim 1, wherein the gene of interest confers a trait selected from the group consisting of herbicide tolerance, insect or pest resistance, disease resistance, increased biomass, modified fatty acid metabolism, modified carbohydrate metabolism, and modified nutritional quality.

4. The construct of claim 2, wherein the DNA cassette and selectable marker gene are operably linked to the same promoter.

5. The construct of claim 2, wherein the DNA cassette and the selectable marker gene are operably linked to different promoters.

6. The construct of claim 2, wherein the selectable marker gene encodes a product selected from the group consisting of CP4 EPSPS, phosphinothricin acetyltransferase, DMO, NptII, glyphosate acetyl transferase, mutant acetolactate synthase, methotrexate resistant DHFR, dalapon dehalogenase, PMI, Protox, hygromycin phosphotransferase and 5-methyl tryptophan resistant anthranilate synthase.

7. The construct of claim 1, wherein the DNA cassette is selected from the group consisting of crtB, gus, gfp, sacB, lux, an anthocyanin synthesis gene, DefH9-iaaM, rolB, OsCDPK2, AP2, AFR2, ANT transcription factor, LEC2, Snf-1, cobA, KAS4, splA, zein inverted repeats, B-peru, and yeast ATP-PFK.

8. The construct of claim 1, wherein the promoter that is functional in a seed is functional in a tissue selected from the group consisting of an embryo, seed endosperm, cotyledon, aleurone, and seed coat.

9. The construct of claim 1, wherein the promoter that is functional in a seed is selected from the group consisting of a napin promoter, a beta-phaseolin promoter, a beta-conglycinin subunit promoter, a zein promoter, an Osgt-1 promoter, an oleosin promoter, a starch synthase promoter, a globulin 1 promoter, a barley LTP2 promoter, an alpha-amylase promoter, a chitinase promoter, a beta-glucanase promoter, a cysteine proteinase promoter, a glutaredoxin promoter, a HVA1 promoter, a serine carboxypeptidase II promoter, a catalase promoter, an alpha-glucosidase promoter, a beta-amylase promoter, a VP1 promoter, a USP, USP88 or USP99 promoter, and a bronze2 promoter.

10. A transgenic plant cell transformed with the construct of claim 1.

11. A transgenic plant transformed with the construct of claim 1.

12. A transgenic plant co-transformed with a first DNA construct and a second DNA construct, wherein the first DNA construct comprises a first DNA segment comprising left and right T-DNA borders flanking a gene of interest operably linked to a promoter functional in plants, and wherein the second DNA construct comprises a second DNA segment comprising a second set of left and right T-DNA borders flanking a promoter functional in a seed operably linked to a DNA cassette that confers a detectable phenotype in seeds comprising the DNA cassette and a marker gene operably linked to a promoter functional in plants, wherein the detectable phenotype comprises a change of: seed size, seed opacity, seed germinability, seed viability, seed shape, or seed texture.

13. A cell of the plant of claim 12, wherein the cell comprises the first DNA construct and the second DNA construct.

14. The DNA construct of claim 1, comprising a right or left T-DNA border flanking the first DNA segment.

15. The DNA construct of claim 14 wherein the construct further comprises a second T-DNA border flanking the second DNA segment.

16. The DNA construct of claim 1, comprising a right or left T-DNA border flanking the second DNA segment.

17. The DNA construct of claim 14, wherein the T-DNA border is a right T-DNA border.

18. The DNA construct of claim 14, wherein the T-DNA border is a left T-DNA border.

19. The DNA construct of claim 1, wherein the detectable phenotype comprises a change of seed shape.

20. The DNA construct of claim 1, wherein the detectable phenotype comprises a change of seed opacity.

* * * * *